(12) United States Patent
Rudge et al.

(10) Patent No.: US 10,531,821 B2
(45) Date of Patent: Jan. 14, 2020

(54) METHOD AND APPARATUS FOR ACQUIRING BLOOD FOR TESTING

(71) Applicant: Neoteryx, LLC, Torrance, CA (US)

(72) Inventors: James Rudge, Torrance, CA (US);
Emmet Welch, Torrance, CA (US);
Yibo Guo, Torrance, CA (US); Allen A Bischofberger, Torrance, CA (US);
Stuart A. Kushon, Torrance, CA (US);
Peter Rahn, Torrance, CA (US)

(73) Assignee: Neoteryx, LLC., Torrance, CA (US)

( * ) Notice: Subject to any disclaimer, the term of this patent is extended or adjusted under 35 U.S.C. 154(b) by 205 days.

(21) Appl. No.: 15/288,842

(22) Filed: Oct. 7, 2016

(65) Prior Publication Data

US 2017/0071520 A1    Mar. 16, 2017

Related U.S. Application Data

(63) Continuation of application No. 13/668,062, filed on Nov. 2, 2012, now abandoned.
(Continued)

(51) Int. Cl.
*A61B 5/15* (2006.01)
*B01L 3/00* (2006.01)
(Continued)

(52) U.S. Cl.
CPC .. *A61B 5/150358* (2013.01); *A61B 5/150022* (2013.01); *A61B 5/150213* (2013.01); *A61B 5/150305* (2013.01); *A61B 5/150343* (2013.01); *A61B 5/150351* (2013.01); *A61B 5/150755* (2013.01); *B01L 3/0275* (2013.01); *B01L 3/50* (2013.01); *B01L 3/5023* (2013.01); *B01L 3/5085* (2013.01); *B01L 9/543* (2013.01); *B01L 2200/0678* (2013.01); *B01L 2300/069* (2013.01);
(Continued)

(58) Field of Classification Search
CPC ................................................ A61B 5/150358
See application file for complete search history.

(56) References Cited

U.S. PATENT DOCUMENTS

| 3,164,279 A | 1/1965 | Towns |
| 3,452,701 A | 7/1969 | Mogayzel et al. |

(Continued)

FOREIGN PATENT DOCUMENTS

| EP | 0283613 A2 | 9/1988 |
| EP | 0940678 A1 | 9/1999 |

(Continued)

OTHER PUBLICATIONS

Japanese Patent Application No. 2010-506506, Office Action dated Jun. 24, 2014, 9 pages.
(Continued)

*Primary Examiner* — Daniel L Cerioni
*Assistant Examiner* — Yasmeen S Warsi
(74) *Attorney, Agent, or Firm* — Stetina Brunda Garred & Brucker; Lowell Anderson

(57) ABSTRACT

A blood sampling device is provided having holder with a manipulating end and an absorbent probe on the opposing end. The probe is of hydrophilic polymer sized to directly absorb a predetermined volume of up to about 30 microliters of blood. Ribs on the holder position the probe within a compartment of a container to prevent contact with the container. The ribs also position the probe within extraction wells.

19 Claims, 15 Drawing Sheets

Related U.S. Application Data

(60) Provisional application No. 61/555,956, filed on Nov. 4, 2011.

(51) Int. Cl.
*B01L 3/02* (2006.01)
*B01L 9/00* (2006.01)
*G01N 1/40* (2006.01)

(52) U.S. Cl.
CPC ............... *B01L 2300/105* (2013.01); *G01N 2001/4027* (2013.01)

(56) References Cited

U.S. PATENT DOCUMENTS

| | | |
|---|---|---|
| 3,620,677 A | 11/1971 | Morison |
| 4,175,008 A | 11/1979 | White |
| 4,635,488 A | 1/1987 | Kremer |
| 4,648,408 A | 3/1987 | Hutcheson et al. |
| 4,648,498 A | 3/1987 | Hutcheson et al. |
| 4,678,757 A | 7/1987 | Rapkin |
| 5,014,718 A | 5/1991 | Mitchen |
| 5,057,282 A | 10/1991 | Linder |
| 5,064,541 A | 11/1991 | Jeng et al. |
| 5,078,969 A | 1/1992 | Nason |
| 5,324,482 A | 6/1994 | Scaramelia et al. |
| 5,418,143 A | 5/1995 | Zweig |
| 5,427,953 A | 6/1995 | Yee |
| 5,494,646 A | 2/1996 | Seymour |
| 5,830,154 A | 11/1998 | Goldstein et al. |
| 5,895,704 A | 4/1999 | Lerch et al. |
| 5,922,614 A | 7/1999 | Cesarczyk |
| 6,036,659 A | 3/2000 | Ray et al. |
| 6,309,887 B1 | 10/2001 | Ray |
| 6,383,804 B1 | 5/2002 | Ward, Jr. et al. |
| 6,524,533 B1 | 2/2003 | Tyrrell |
| 7,374,723 B2 | 5/2008 | Wuske et al. |
| 7,611,670 B2 | 11/2009 | Wandell et al. |
| 7,686,681 B2 | 3/2010 | Di Luccio et al. |
| 8,141,717 B2 | 3/2012 | Wingo et al. |
| 8,852,122 B2 | 10/2014 | Mao et al. |
| 8,920,339 B2 | 12/2014 | Mao et al. |
| 2003/0045814 A1 | 3/2003 | Sangha |
| 2003/0119202 A1 | 6/2003 | Kaylor et al. |
| 2005/0009200 A1 | 1/2005 | Guo et al. |
| 2005/0227269 A1 | 10/2005 | Lloyd, Jr. et al. |
| 2005/0252820 A1 | 11/2005 | Sanchez-Felix et al. |
| 2006/0229530 A1 | 10/2006 | Hosoda et al. |
| 2008/0060424 A1 | 3/2008 | Babic et al. |
| 2008/0249487 A1 | 10/2008 | Engvall |
| 2011/0004122 A1 | 1/2011 | Sangha |
| 2011/0224579 A1 | 9/2011 | Maas et al. |
| 2013/0116597 A1 | 5/2013 | Rudge et al. |

FOREIGN PATENT DOCUMENTS

| | | |
|---|---|---|
| EP | 1712180 A1 | 10/2006 |
| EP | 2128617 A1 | 12/2009 |
| JP | 63215939 | 9/1988 |
| JP | 05503230 | 6/1993 |
| JP | 05187976 | 7/1993 |
| JP | 09190796 | 7/1997 |
| JP | 11076213 | 3/1999 |
| JP | 2005017280 | 1/2005 |
| JP | 2005055216 | 3/2005 |
| JP | 2005283366 | 10/2005 |
| JP | 2008521019 | 6/2008 |
| WO | 199502996 A1 | 2/1995 |
| WO | 2005018803 A1 | 3/2005 |
| WO | 2010114976 A1 | 10/2010 |
| WO | 2010127059 | 11/2010 |
| WO | 2012145379 A1 | 10/2012 |
| WO | 2012145390 A1 | 10/2012 |

OTHER PUBLICATIONS

U.S. Appl. No. 14/254,325, Notice of Allowance dated Aug. 7, 2014, 11 pages.
International Search Report for PCT/US12/63586 filed Nov. 5, 2012 for applicant James Rudge.

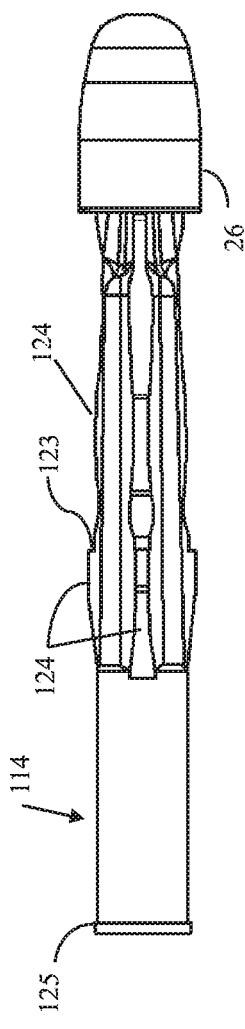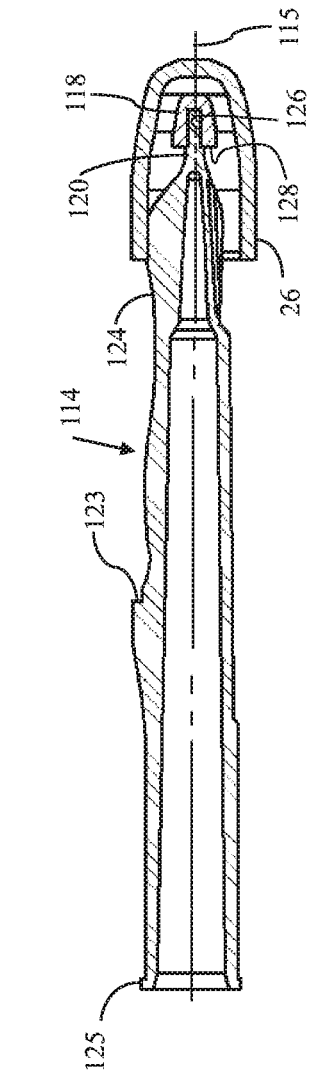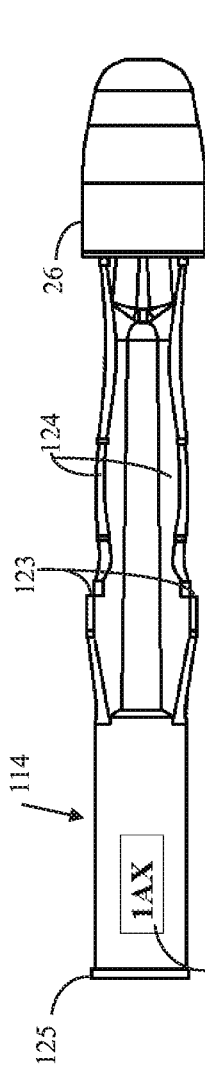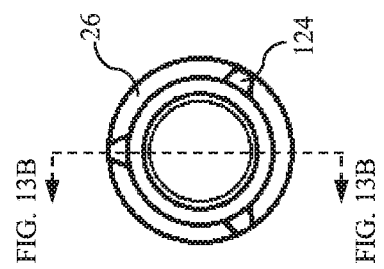

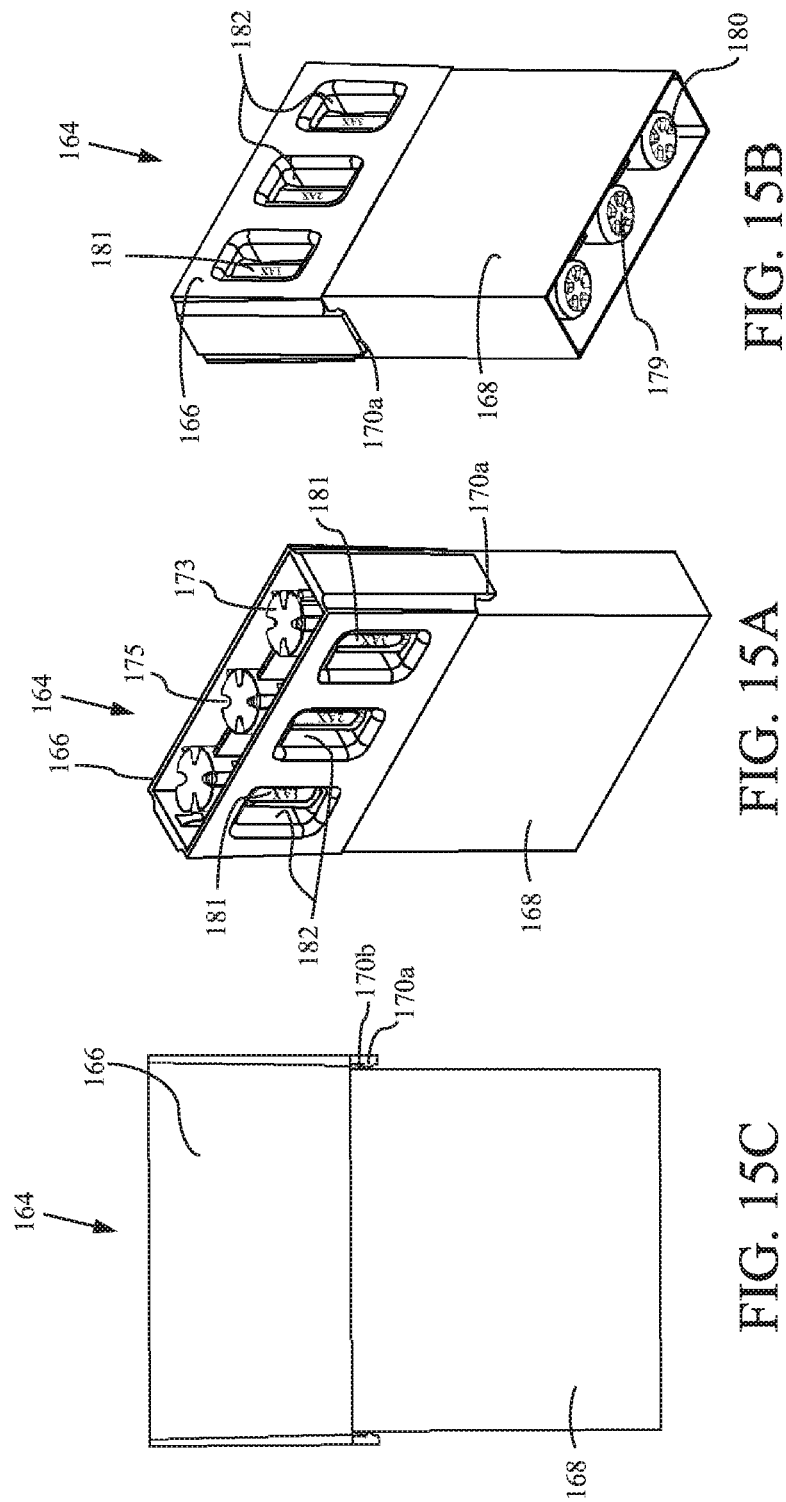

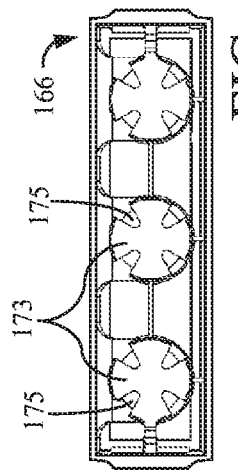
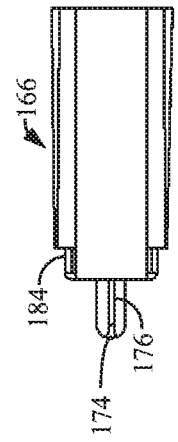
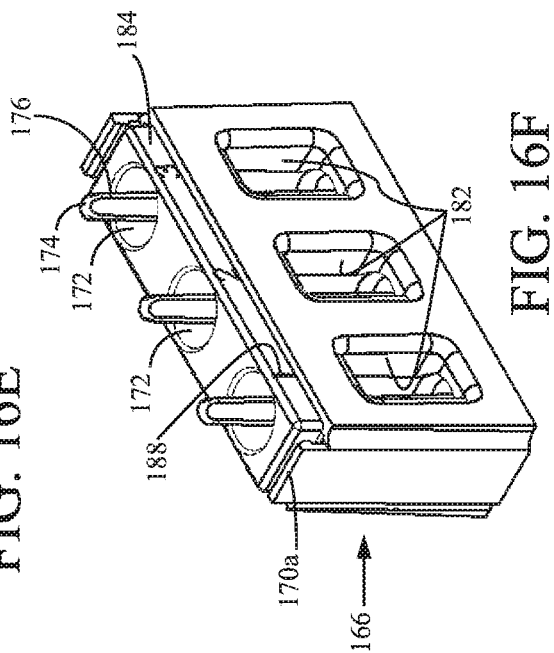
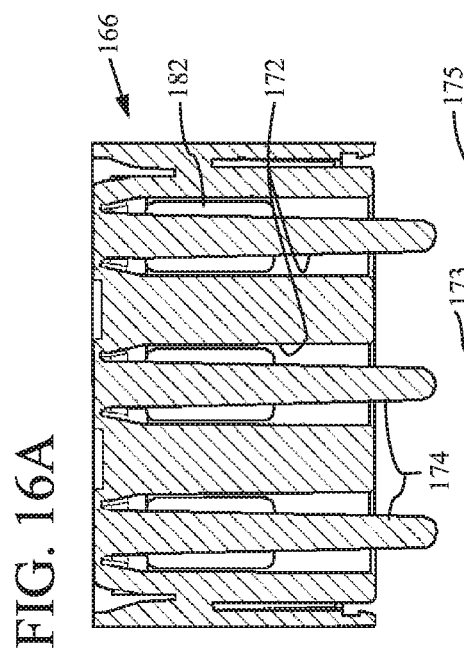
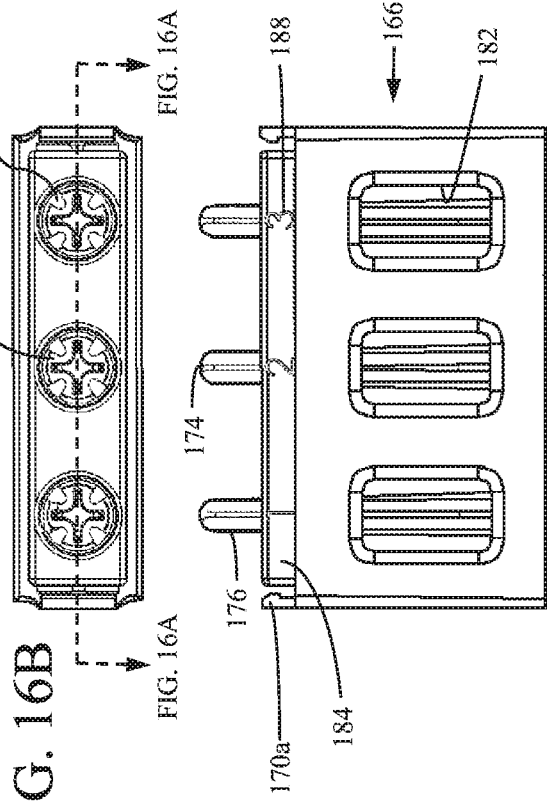

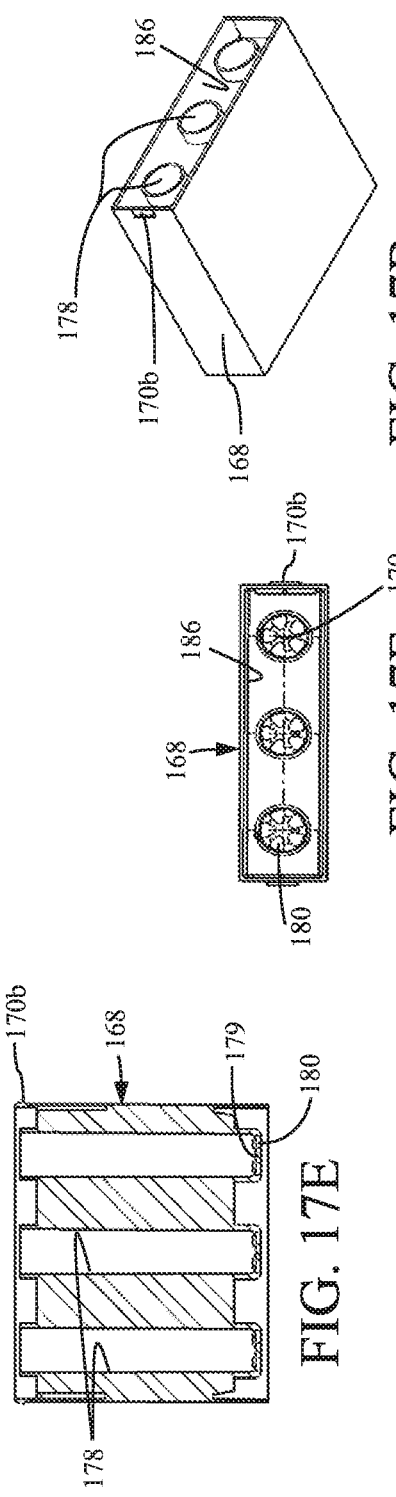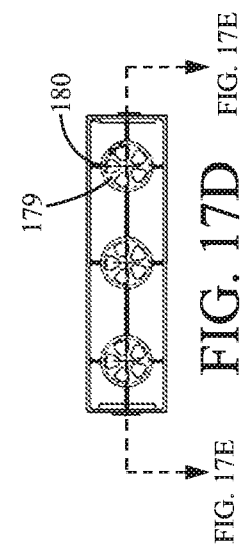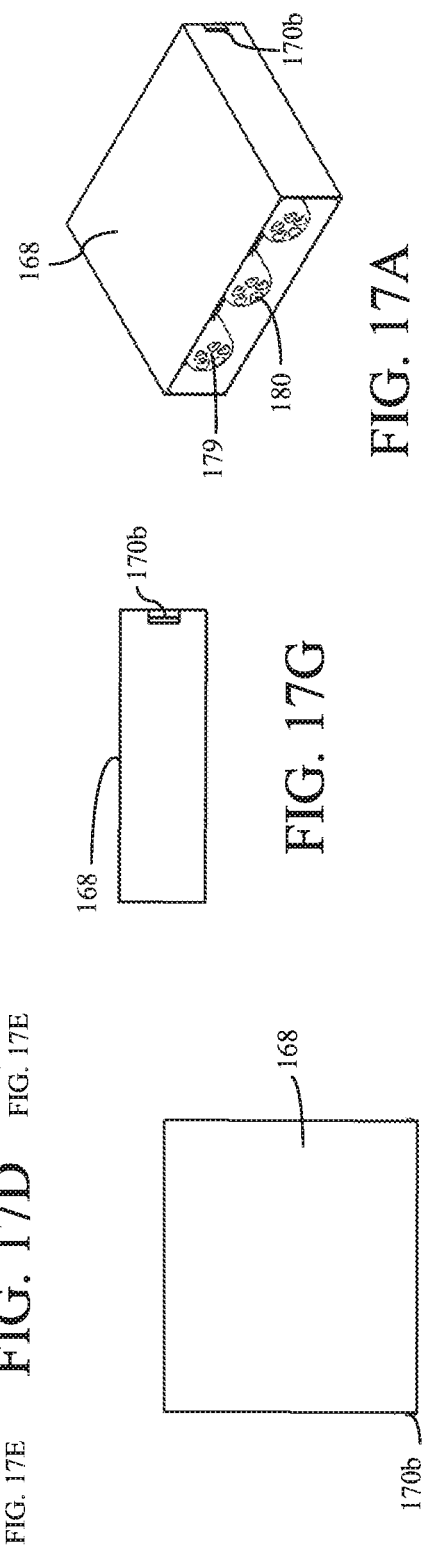

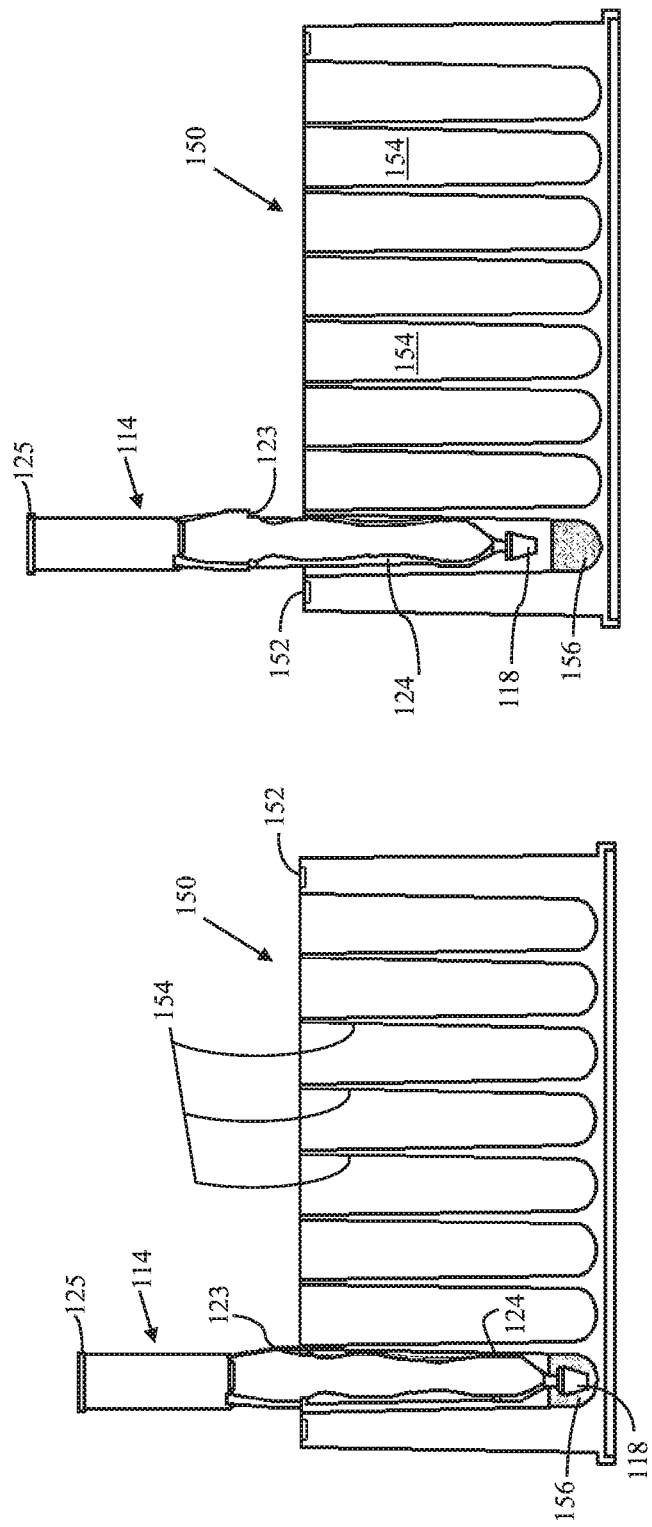

METHOD AND APPARATUS FOR ACQUIRING BLOOD FOR TESTING

CROSS-REFERENCE TO RELATED APPLICATIONS

The application claims the benefit under 35 U.S.C. § 119(e) to Provisional Patent Application No. 61/555,956 filed Nov. 4, 2012, titled METHOD AND APPARATUS FOR ACQUIRING BLOOD FOR TESTING, the entire contents of which are incorporated herein by reference.

BACKGROUND OF THE INVENTION

This application relates to a method apparatus for sampling blood for use in testing for either research or for diagnostic use.

Multiple blood samples are used for clinical trials for pharmacokinetic analyses. These samples are often collected by sampling whole blood freezing and then processing the frozen blood later. Frozen blood requires a 200-250 ul sample of blood to be taken. This sample size limits the number of time-points which can be taken from a single animal due to the limited blood volume of small animals such as rats. Furthermore small volumes of blood samples are desired when dealing with critically ill patients. Moreover, there are high costs involved with the freezing transportation and processing of whole blood.

Blood samples are also collected using a bloodspot technique which requires smaller sample volumes, typically 45-60 ul for humans and 15 ul for rats, although evolving analytical techniques are using samples using 10-15 ul of human blood and smaller. Referring to FIG. 1, samples are taken from the subject usually by 'finger pricking' the individual and then sampling the evolved blood using a glass capillary 5. Once a desired quantity of blood is taken (45-60 ul) then the blood from the capillary 5 is carefully transferred to a 'blood spot card' 7 such as Watman's FDA Eulte, using 15 ul aliquots spots across four spots. Care must be taken not to contaminate the card and not to touch the card with the capillary except for the pre-designated portions where the sample is to be deposited. After blood is taken and spotted, a known concentration of an internal standard is sprayed onto the spotted card and then accurately punching disks (2-6 mm diameter) out of the blood spot or multiple blood spots. Once sampling is complete, the cards 7 are dried in air before transferring or mailing to labs for processing. Because the blood is dried, not only do some enzymatic processes cease preventing further breakdown before testing or during storage, but dried blood is not considered hazardous and no special precautions need be taken in handling or shipping. Once at the analysis site, circular discs containing the dried blood are punched out of the card and the internal standard and drug (and/or metabolite) are extracted from the disks into a supernatant which is then analyzed usually by liquid chromatography mass spectrometry.

When a card is used for direct sample collection from a wound (e.g. a neonatal heel prick or a finger prick) there is risk for collection of too much blood on the card which will lead to an overlapping of samples from the spots. Additionally, if blood flow is insufficient a non-homogenous sample can be collected (multiple small spots instead of a single large spot). This will lead to difficulty in obtaining a subpunch from the card that is representative of the entire spot. Additionally, various chemical treatments of card materials can lead to separation of the PCV and serum during the drying process leading to non-homogenous sampling.

There are drawbacks, however, to the downstream processing of blood spots. One is in the area of sample quantitation. It is difficult to sample precise volumes using traditional glass capillaries, particularly directly from an animal or patient blood bolus. Air bubbles in capillaries can result in different capillary volumes being deposited on the cards, leading to different volumes when the card is punched. While use of micropipettes (15 ul sample) can successfully create accurate spot volumes in carefully controlled settings, in practice these have proven to be unreliable.

Another drawback with the punching technique is that it relies on a constant sample viscosity in the expectation that the sample will spread uniformly on the sample card. A constant viscosity results in blood spot diameters remaining constant when equal volume samples are administered to the cards. Unfortunately, viscosity varies significantly because of differing hematocrit (Ht or HCT) or packed cell volume (PCV) levels in the blood. Samples with high hematocrit levels form smaller diameter spots on the bloodspot papers, leading to different concentrations of blood within the fixed diameter of the spots sampled. PCV levels are believed to show around a 45% variance in spot diameters. As internal standards are sprayed onto the spotted blood this could result in a 45% error in quantitation. A further problem is that the blood is placed in marked areas on the cards, but often the person sampling the blood misses the mark and blood goes outside the marked area, making it difficult to accurately locate the circular punch over the blood spot. Even if the blood spot is centered in the card, the person punching the card may not center the punch, resulting in variable sample size. Further, the punching often shears the card and that often shakes dried blood loose, and if the punch cuts across a portion of the blood spot that also causes dried blood to be ejected into the air or work area.

Moreover, the blood spots are placed on rectangular cards which are difficult to manipulate by automated equipment, thus requiring extensive, expensive and time consuming manual handling and processing. Automated handling equipment can be acquired for the specially shaped cards, but it is custom made, expensive, and of limited application.

There is thus a need for an improved method and apparatus for use in blood sampling that reduces or eliminates one or more of the above errors and difficulties.

SUMMARY

A device is provided that is suitable as a quantitative sampling tool for biological fluids, preferably blood. It is designed for samples to be easily dried, shipped, and then later analyzed. The device includes an absorbent probe, preferably smaller at a distal end and larger at a fastening end, has its fastening end fastened to a holder and its other, distal end free to contact a fluid to be absorbed, such as blood. The holder allows easy manipulation of the absorbent probe. The absorbent probe is placed against a blood sample or blood drop(s). Wicking action draws the blood into the absorbent probe. An optional barrier between the absorbent probe and holder stops blood passing to the holder or wicking to the holder. The absorbent probe is made of a material that wicks up substantially the same volume of fluid even when excess fluid is available. The volume of the absorbent probe affects the volume of fluid absorbed. A hydrophilic polymeric material is believed suitable for the absorbent probe, with polyolefin believed especially suitable for use.

The absorbent probe is advantageously shaped with an exterior resembling a truncated cone with a narrower and rounded distal end and the wider end is fastened to the holder. Advantageously the holder has a cylindrical post that fits into a recess inside the center of the absorbent probe and extending along the longitudinal axis of the probe and holder. Thus, the truncated conical shape has thick sidewalls that abut the post on the holder, with a distal tip joining the sidewalls and forming the distal end of the probe.

The holder is preferably, but optionally adapted for use with a pipette because a variety of automated equipment exists to hold and manipulate pipettes. Thus, a tubular holder is preferred, especially one that can fit over the end or tip of a pipette for easy manipulation. A tubular, conical shaped holder is thus preferred, with the absorbent probe on the narrow, tip end of the holder. The wider holder end is open to fit onto a pipette tip. The holder may have outwardly extending flanges located to abut mating structures in holders, drying racks or test equipment to help position the absorbent probe at desired locations in such holders, drying racks and test equipment.

The conical shape of the absorbent probe helps wick the sample quickly and uniformly. Preferred sampling time is desirably as short as possible with about 2 seconds (less if possible) being most preferred, and up to 15 seconds being acceptable for some applications. Maintaining the probe in contact with the sample blood droop for between about 2-10 seconds is thus believed sufficient, with a contact time of about 2-5 seconds preferred, and a contact time of about 2 seconds (preferably less) being most preferred, and contact times of 5-10 seconds much less preferred. The contact time is desirably as short as possible. The probe absorbs a predetermined volume of blood during that time, and once saturated does not absorb more blood. The size and shape of the probe can be varied to adjust the volume of absorbed blood and the rate of absorption. Blood volumes of about 7-15 µL are believed suitable, but volumes of about 20 µL and even up to about 30 µL are believed desirable for some applications.

After absorbing a sample, the absorbent probe is then dried, preferably for about 2-3 hours, ideally about 2 hours or less. But the time will vary with the humidity, temperature, volume to be dried and the shape and configuration of the absorbent probe. Drying can be done on a suitable rack or holder, or preferably the absorbent probe and holder can be transferred to a special drying container configured to help drying while minimizing the contact between the probe and the walls of the drying container or other potential contaminant surfaces. As desired, the drying container may have a desiccant to facilitate drying. The drying container may also provide a protective cover or housing which may be sealed for transport to prevent contamination. The cover advantageously has a surface onto which printed indicia may be written to identify the blood sample and provide related information or other information as desired. Advantageously, the preferred dimensions of the container, and the relative positions of the holders within the container, will conform to SBS Microwell plate specifications.

Upon receipt at the location where the testing is to occur, the absorbent probe is placed in a predetermined volume of liquid solvent by hand or by liquid handling robot to extract the analytes of interest from the dried blood. Physical agitation techniques such as sonication or vortexing of the fluid and/or the absorbent probe can accelerate the extraction analytes of interest from the dried blood into a liquid sample matrix. The fluid is separated from the absorbent probe for further processing (e.g., concentrating), or analysis (e.g., HPLC or GC analysis), while the absorbent probe may be discarded. Physical separation techniques such as centrifugation, evaporation/reconstitution, concentration, precipitation, liquid/liquid extraction, and solid phase extraction can be used to further simplify the sample matrix for further analysis (e.g. HPLC or GC analysis)

There is thus advantageously provided a blood sampling device that includes an absorbent probe made of a hydrophilic polymeric material of sufficient size to absorb a maximum of about 20 µl of blood in about 2-5 seconds and having a length of less than about 5 mm (0.2 inches) and a cross-sectional area of less than about 20 mm$^2$ and a density of less than about 4 g/cc. The probe is connected to a holder having a manipulating end opposite the probe.

In one embodiment the holder may include a pipette tip or a tapering, tubular structure configured to nest with a pipette tip. The probe is preferably made of polyethylene, and both the probe and holder are made under aseptic conditions, or terminally sterilized. Unsterilized probes are also believed suitable for some applications. The probe may contain dried anti-coagulant, and after use contains dried blood. The holder preferably has a plurality of ribs extending along a length of the holder. The ribs may have a height and length selected to keep the probe from contacting walls of a recess into which the holder and probe are placed for shipment or for extraction of the dried blood in the probe.

The holder preferably has a hollow end opposite the probe and the container may have a first portion with a mounting projection portion sized to fit into and releasably engage the hollow end of the holder. The container preferably has a second portion releasably fastened to the first portion and having a recess configured to enclose a portion of the holder for transportation of the holder. The container advantageously has a plurality of openings allowing air to access the probe. Moreover, the first portion may have a side with an access port therein of sufficient size and located so that indicia may be applied through the port and onto the holder when the holder is on the mounting projection.

Advantageously there are a plurality of holders each with a probe, with each of the plurality of holders having a hollow end opposite its probe. The container likewise has a plurality of elongated mounting projections each sized to fit into and releasably engage one of the hollow ends of the plurality of holders. The second portion of the container has recesses configured to separately enclose each of the plurality of holders in a separate enclosure within the container. Preferably, the plurality of the holders each has a plurality of ribs extending along a length of the holder with the ribs configured to keep the probe from contacting walls of the container. As desired, a desiccant may be placed inside the container to help dry the blood in the probe or keep the blood dried. Each holder may have visible indicia associating the holder with the container and with at least one other holder, such as serial numbers with various portions of the number indicating related holders/probes and the container in which the holders are shipped.

There is also provided a kit for testing blood. The kit includes a plurality of elongated holders each having a manipulating end and opposite thereto an absorbent probe made of a hydrophilic, polymeric material configured to absorb 30 microliters or less of blood within about 5 seconds or less, although the volume and time can vary. The kit also includes a container having a plurality of compartments. Each compartment is configured to releasably receive one of the elongated holders and its associated probe. The container and holder are configured to prevent the probes from abutting the compartment within which the holder and probe are placed. The container has openings in each compartment to allow air to enter each of the compartments and reach the probe within the compartment with which the openings are associated.

In further variations the kit may include a plurality of access ports with each port associated with a different one of the compartments. Each port is located to allow printing onto the manipulating end of the holder in the compartment with which the port is associated. At least some of the holders preferably have a plurality of ribs extending along a length of the holder with the ribs located between the manipulating end and the probe. The ribs cooperate with the container to prevent the probe from abutting the compartment within which said ribbed holder is placed. The container preferably has two parts cooperating to form tubular shaped compartments. The container may have a first part with a plurality of elongated mounting protrusions each extending along a portion of a different compartment. The manipulating end of the holder is hollow with the hollow end fitting onto the mounting protrusion to releasably fasten the holders onto the mounting protrusions.

The kit may include visible indicia on a plurality of holders and the container with the indicia associating the holders with at least one of the container or another holder within the container. The probes are preferably made of polyethylene and configured to absorb about 1-7 microliters of blood, preferably within 1-7 seconds, and more preferably within about 1-5 seconds. Advantageously, at least one holder is tubular throughout its length and the probe on that holder is held within one end of the tubular holder. The probe may contain one or more of dried blood, dried anticoagulant or an internal standard. To help drying and maintain a dried probe, at least one of the compartments may contain a desiccant.

There is also provided a method or process for use in testing a blood sample. The method includes placing an absorbent probe in physical contact with a blood sample. The probe is made of a hydrophilic polymeric material and connected to a holder. The method also includes maintaining the probe in contact with the blood sample until a predetermined amount of blood is absorbed by the probe. The probe is removed from contact with the blood and the probe and blood are dried, without contaminating the blood.

In other variations, the probe is configured to absorb a predetermined amount of blood of about 5-15 microliters and the probe absorbs each volume within that range of blood volumes in less than seven seconds and preferably within less than about five seconds. Advantageously, the blood sample is on a live animal when contacted by the probe and obtained directly from a fresh wound. One preferred absorbent probe has a volume of about 35 mm$^3$, to and absorbs about 13-14 microliters of blood in about 3 seconds, and will absorb 9-10 microliters of blood in about 2.5 seconds. The pore volume of the probe is about 38%. Another preferred probe has a volume of about 24 microliters, a density of about 0.6 g/cc and will absorb about 10 microliters of blood in about 2.5 seconds. This probe has a pore volume of about 40%.

The process may also include placing the probe with the dried blood in a compartment within a container, or placing the probe with wet blood in the container where the blood dries. The method also includes placing the absorbent probe with dried blood in a pipette tip. The probe with dried blood is eventually placed in a container along with fluid selected to reconstitute the dried blood in the probe. Preferably the process uses a plurality of probes, each held in a pipette tip and each containing dried blood, with the pipette tips being held in a tray for extraction of the dried blood.

The holder may include a plurality of ribs configured to prevent the probe from contacting at least one of the walls of a shipping container in which the holder is placed or the walls of a recess in which the probe is placed to extract the dried blood. The process may provide the holder with a position stop located to position the probe within at least one of a container or a well plate so as to prevent the probe from contacting the container or well plate.

BRIEF DESCRIPTION OF THE DRAWINGS

These and other advantages and features of the invention will be better appreciated in view of the following drawings and descriptions in which like numbers refer to like parts throughout, and in which:

FIG. 13A is a bottom elevation view of a further embodiment of a holder having an optional protective sheath thereon;

FIG. 13B is a sectional view of the holder of FIG. 13A, taken along section 13B-13B of FIG. 13D;

FIG. 13C is a top elevation view of the holder of FIG. 13A;

FIG. 13D is a left side elevation view of the holder of FIG. 13C;

FIG. 15B is a bottom perspective view of the container of FIG. 15A;

FIG. 15C is a side elevation view of the opposing side of the container shown in FIG. 15A;

FIG. 16A is a sectional view of the top portion of the container of FIGS. 15A and 16F, taken along section 16A-16A of FIG. 16B FIG. 16B is a top elevation view of the top portion of the container of FIGS. 15B and 16f;

FIG. 16C is a side elevation view of the container top of FIGS. 16B and 16F;

FIG. 16D is a bottom elevation view of the container top of FIG. 16F;

FIG. 16E is a side elevation view of the container top of FIGS. 16B and 16F, with the opposing side being a mirror image thereof;

FIG. 16F is a perspective view of the container top of FIG. 15A;

FIG. 17A is a bottom perspective view of the lower portion of the container of FIG. 15B;

FIG. 17B is a top perspective view of the lower container portion of FIG. 17A;

FIG. 17C is a side elevation view of the lower container portion of FIG. 17A;

FIG. 17D is a bottom elevation view of the lower container portion of FIG. 17C;

FIG. 17D is a sectional view of the lower container portion taken along section 17E-17E of FIG. 17D;

FIG. 17F is a top elevation view of the lower container portion of FIG. 17D;

FIG. 17G is a side elevation view of the lower container portion of FIG. 17D, with the opposing side being a mirror image thereof;

FIG. 20A is a sectional view of a well plate with a holder positioned so its absorbent probe is in extraction fluid; and FIG. 20B is a sectional view of the well plate of FIG. 20a with the holder positioned so its absorbent is near to but not in the extraction fluid.

DETAILED DESCRIPTION

Figure 8:
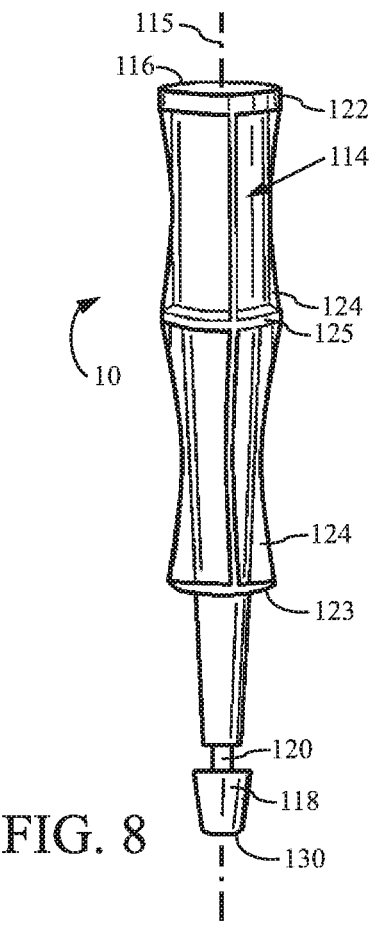
FIG. 8 is a side view of a holder having outwardly extending ribs for manipulation and a truncated, conical-shaped absorbent probe.

Referring to FIGS. 2-3 and 8, a collection device 10 for collecting various fluids, especially biological fluids and preferably blood, is provided. The device 10 has a sampling end 12 and a holder 14 joined at a juncture 16. The sampling end 12 advantageously comprises an absorbent probe 18 made of a material that wicks up or otherwise absorbs a sample 20 from a fluid source 22, which preferably comprises body fluids and more preferably is blood from a finger-prick or cut 23. The holder 14 may have the absorbent material 18 held in one end, with an opposing end either closed, or preferably open and hollow and optionally configured to allow it to mate with a pipette tip. Releasable adhesives can be used to more securely fasten the parts, but it is believed preferable to force the absorbent probe 18 into a slightly smaller opening in the holder 14 (pipette tip) so the interference fit between the opening and absorbent probe 18 hold the parts together. The device 10 is suitable as a quantitative sampling tool for biological fluids, preferably blood. It is designed for samples to be easily dried, shipped, and then later analyzed.

The juncture 16 is optionally configured to stop wicking of the blood sample 20 past juncture 16, or at least stop wicking adjacent the surface of the absorbent probe 18 at the juncture 16. The absorbent probe 18 thus ends at the juncture 16. The concern is that sample 20 (e.g., blood) will pool inside the holder 14 and not dry out with the sample 20 contained in the remainder of the absorbent probe 18. The juncture 16 preferably comprises a non-porous barrier. It is believed that compressing the outer surface of the absorbent probe 18 at the juncture 16 will restrict wicking by compressing the probe material and thus stop or sufficiently wicking of the fluid sample 20 past the juncture or at least restrict wicking sufficiently to avoid pooling. The juncture 16 could be provided by placing a physical barrier such as wax or plastic between the absorbent probe 18 and the remainder of the sample end 12 and holder 14. The juncture 16 could be formed by joining the absorbent probe 18 to a holder 14 made of material which resists wicking, such as a plastic pipette tip. Various other mechanisms for fastening the absorbent end 18 to the holder 14 will be apparent to one skilled in the art given the present disclosure.

The holder 14 is large enough so a lab technician can manually hold and manipulate the device 10. The holder may take various shapes and is preferably configured to work with tools designed to manipulate pipette tips. By locating the sampling end 12 and its absorbent probe 18 at one end of the holder 14, the user can more easily grip the holder with much less risk of inadvertently touching the blood sample on absorbent probe 18. Further, all portions of the holder 14 can be grabbed by the user or automated equipment, in contrast to the prior art devices which were held by the edges to avoid contamination. Advantageously, the holder 14 is large enough for instruction or cautionary information to be displayed on the holder, such as cautioning the user not to touch the absorbent probe 18.

Figure 1:
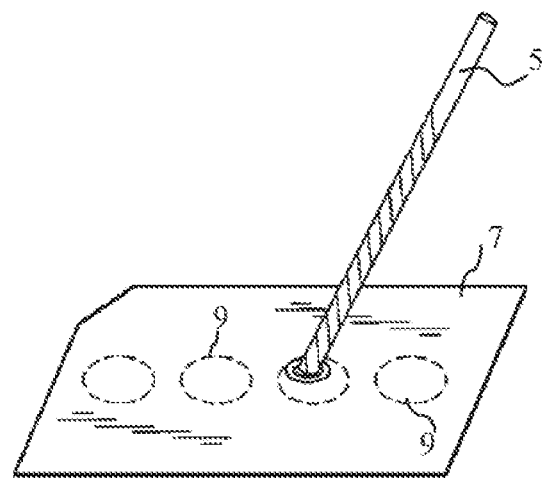
FIG. 1 shows a prior art blood spot card with an aliquot being applied to the card from a capillary tube.
Figure 2A:
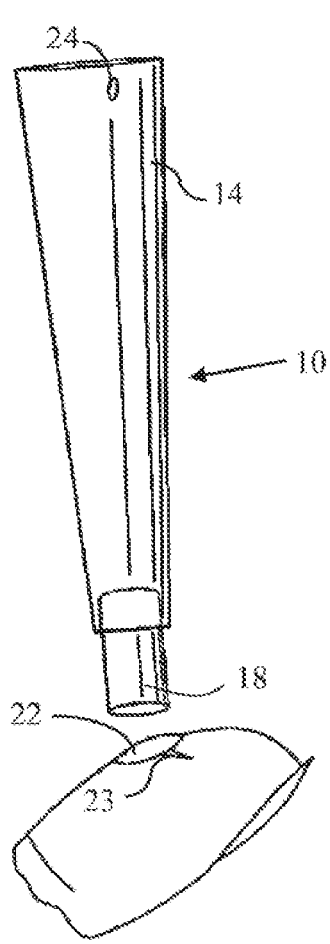
FIGS. 2A and 2B show an absorbent probe before and after directly contacting a fluid, such as blood, at its source on an animal, such as a human finger.
Figure 2B:
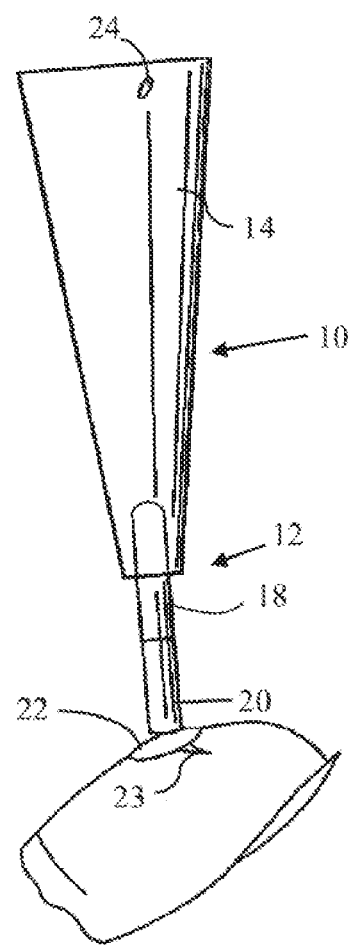
Figure 3A:
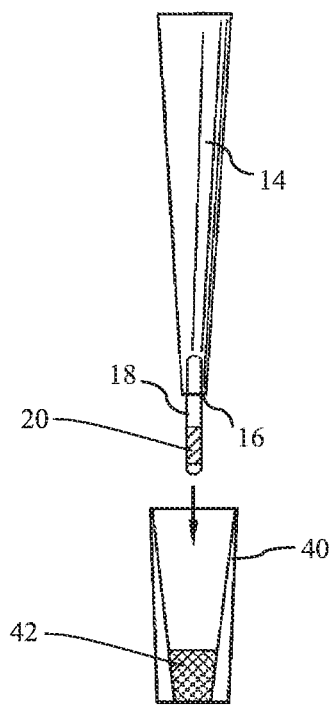
FIGS. 3A and 3B show an absorbent probe and absorbed sample before and during placement in a container with extraction fluid therein.
Figure 3B:
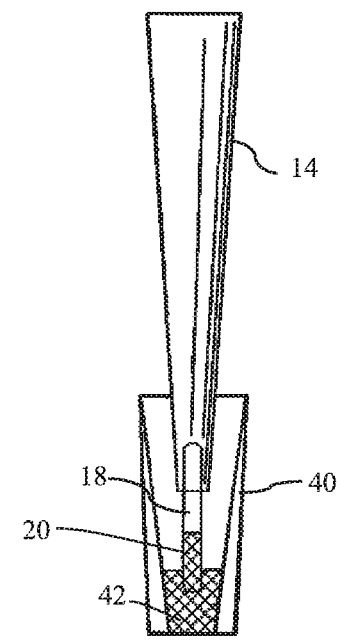
Figure 4A:
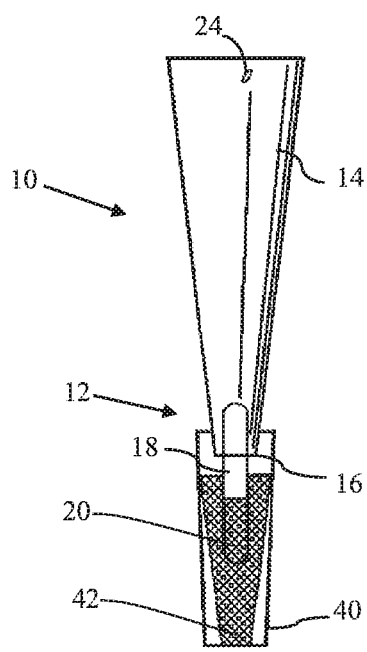
FIGS. 4A and 4B show the absorbent probe of FIGS. 3A, 3B before and after the fluid sample is extracted from the absorbent probe.
Figure 4B:
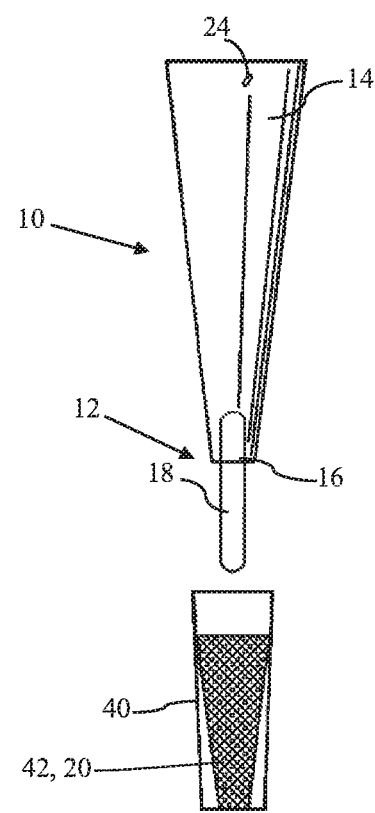
Figure 10:
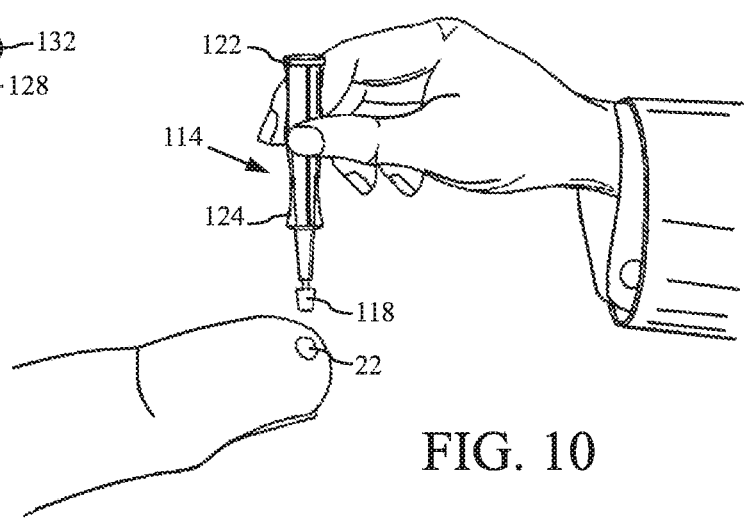
FIG. 10 is an illustrative view of the holder and probe of FIG. 8 ready to contact and absorb a sample from a subject.

In use, the laboratory technician grabs the holder 14 and places the absorbent material 18 in contact with a fluid source 22 as shown in FIGS. 2A, 2B and 10. The absorbent probe 18 absorbs a fluid sample 20 from the fluid source 22 and wicks the sample it into the absorbent probe 18. The absorbent probe 18 is sized or configured to absorb a predetermined volume of blood before saturation. The absorbent probe 18 has exposed on all sides located outside of the holder 14 so that any exposed surface of the probe 18 may be used to absorb fluid. Excess volumes of sample blood 22 will not be absorbed and will drop off or can be gently shaken off of absorbent probe 18. When the fluid sample 20 is absorbed into sample end 12 then the user preferably places the device 10 in a rack for drying. If a single device 10 is used, the holder 14 can be placed on a book or edge of a table with the sample end 12 suspended in air for drying. If multiple devices 10 are used, a rack with a number of generally horizontal shelves or pairs of posts can be used to hold a plurality of holders horizontally for drying, much like the current racks used with the devices of FIG. 1. Alternatively, well trays exist for holding multiple pipette tips and those could also be used.

The orientation of holders 14 and absorbent probe 18 can be alternated so every other sample end 12 extends from one side of the rack to help avoid contact. Alternatively, the holders 14 could be provided with openings 24 to allow the holders 14 to be hung vertically, with the sample end 12 hanging downward from variously configured hangers. The fluid sample 20 in the absorbent probe 18 is preferably thoroughly dried in order to avoid problems arising from shipping wet biological materials. A drying time of about two hours or more in an ambient, room temperature laboratory environment is believed suitable for a sample volume of about 10-15 μl of blood. Drying times of 2-3 hours are believed suitable. Shorter drying times are desirable, but care must be taken to avoid contamination, as may occur by blowing room air onto the samples to dry them faster. The absorbent probe 18 is positioned so that it does not contact other items or otherwise become contaminated, with special care taken to avoid contamination by materials that could affect the results of the analysis of the sample 20. As desired, the holder and probe 18 may be placed into a container for drying as described later. The probes 18 and container may be placed in a plastic bag along with a desiccant to assist drying and either shipped that way, or shipped after the desiccant is removed.

Referring to FIGS. 7 and 13A-13C, an optional protective sheath 26 can be removably placed over the absorbent probe 18 (118) and releasably fastened to holder 14 (114). For example, a tubular sheath 26 with an open end and closed end can have the open end placed over the absorbent probe on sample end 20. An inward facing flange 28a on or adjacent to the open end can releasably engage an outwardly extending flange 28b on the holder 14 to form a snap fit. A threaded connection could also be used instead of the snap fit flanges 28a, 28b. Either configuration works well with holders 14 comprising tubular pipettes or conical pipette tips. Other means of releasably fastening a protective sheath to the holder 18 could be used, including a covered tray configured to hold a plurality of holders 14.

Figure 5:
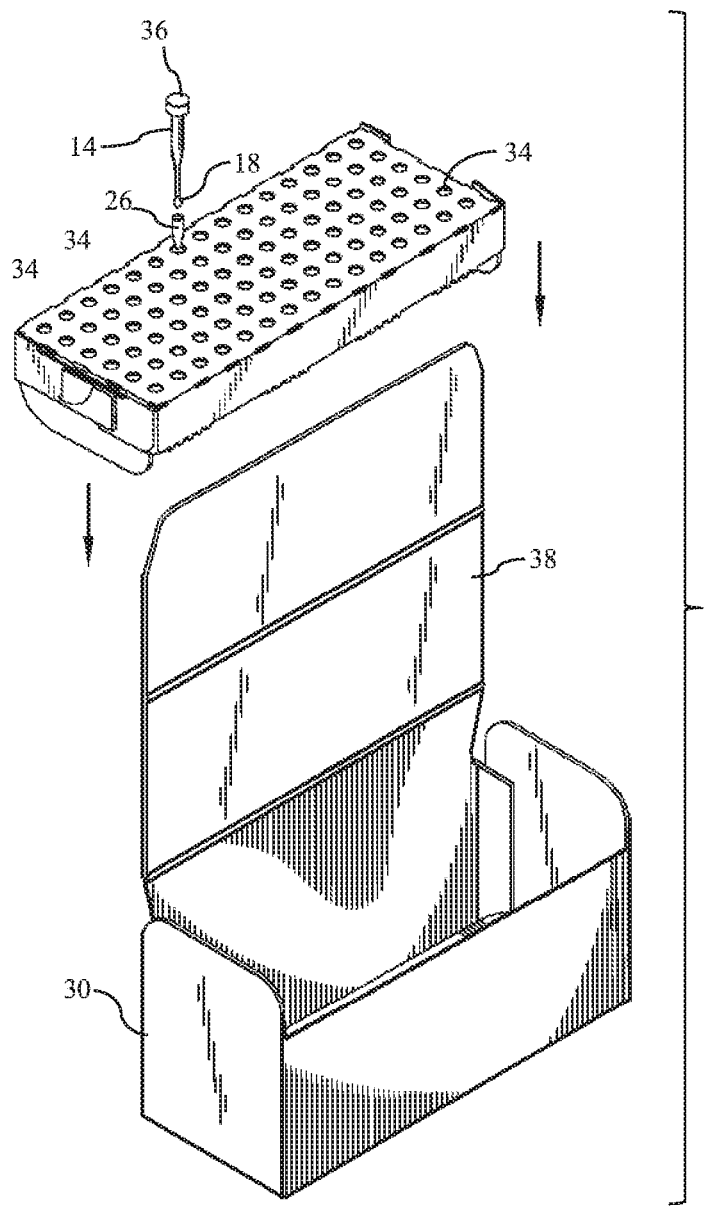
FIG. 5 is an exploded perspective view of an absorbent probe, a tray to hold a plurality of absorbent probes and a covererable case to hold the tray.
Figure 6A:
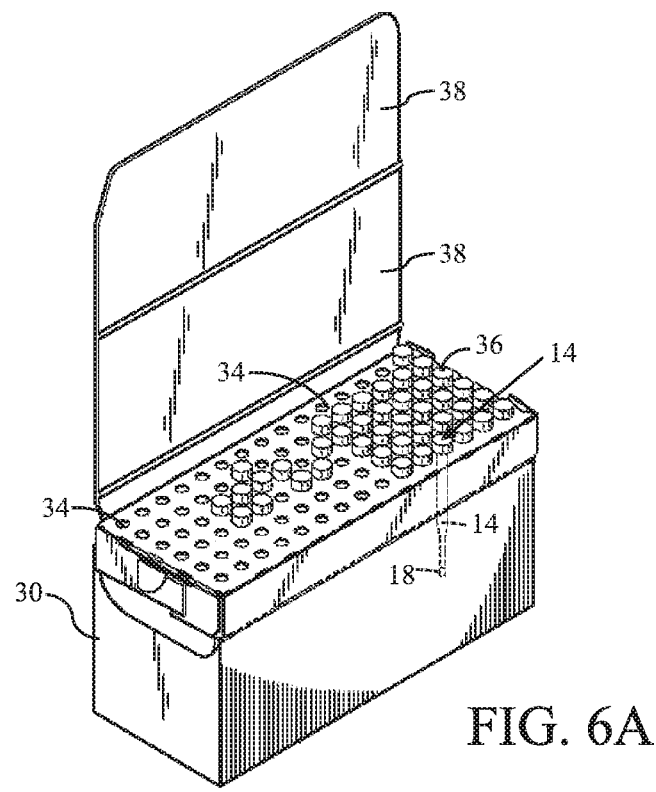
FIGS. 6A and 6B are perspective views of the tray of FIG. 5 inserted into the container with a container lid open and closed.
Figure 6B:
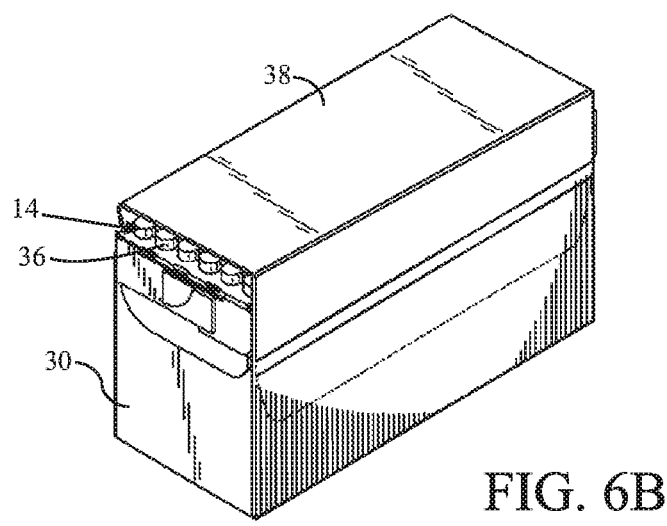

Referring to FIGS. 5-6, the device 10 is preferably contained in a case 30 for transportation. The case 30 may be an expandable container or envelope which is larger than the device 10 and unfolds to allow access to and removal of the device 10 for use, and after the fluid sample 20 is dried allows the device 10 to be placed inside the case 30 which is refolded, sealed and shipped to a laboratory for testing. The container or case 30 and the holders 14 within the container will typically have a human readable label to indicate the container in which each holder belongs. Advantageously, the inside surface of case 30 or the outer surface of case 30 has a writing surface onto which information related to the sample can be placed. Such information could include information for a clinical trial such as code names numbers, barcodes, and RF tags. The name and other information on the subject from which the blood sample is taken, date information, the nature of tests to be conducted, and the project for which the testing is performed. Optionally, a desiccant or moisture absorbing material (not shown) may be placed inside the case 30 for shipping or for storage in order to reduce moisture content and reduce bacteria growth.

Ideally, the case 30 and each device 10 within the case 30 are assigned serial numbers that correspond. Thus, for example, if case 30 contains three devices 10 with blood from a single patient, each device 10 will have a series of common numbers, letters or both indicating they are from the same case and same patient. This labeling helps to associate the device 10 with the appropriate case 30 and its individual holders if they are separated in the laboratory or during analysis. Three devices in a case 30 is believed advantageous since one may be analyzed, one may be used as a backup if there are errors or inconsistencies in initial testing, and one may be used for future verification or retesting, with a series of common numbers, letters etc. making it easier to confirm the devices correspond to the same subject or patient.

Referring to FIGS. 3A, 3B, 4A, 4B, the devices 10 are usually sent to testing laboratories where, upon receipt, the absorbent probes 18 are tested or analyzed while on the holder 14, or where the probes 18 are removed from holders 14 and reconstituted for testing or analysis. The absorbent probes 18 containing dried samples 20 are placed in containers 40 such as test tubes in which a reconstituting fluid 42 is placed. A plurality of containers 40 may be provided in various racks (FIG. 5) configured to hold the containers. Reconstituting fluid is preferably an extraction fluid or solvent selected to remove the analyte from the dried sorbent tip 18. The fluid 42 varies with the nature of sample 20 and the nature of the test to be performed. The absorbent probes 18 can be removed by various manual and automated means, including pulling the absorbent probe out of the holder with tweezers, or by applying air pressure to the inside of a tubular holder 14. Various means for applying air pressure to a pipette in order to expel the contents of the pipette are also known, and those ways are equally applicable blowing the absorbent probe 18 out of the opening in a pipette tip or other tubular container. The container 40, absorbent probe 18 and its sample 20 are typically agitated to reconstitute the (dried) sample 20 and transfer it to the reconstituting fluid 42 and out of the absorbent probe 18. Sonication or vortexing may be used to agitate the reconstituting fluid 42 and expedite the transfer of the sample 20 from the probe 18 to the fluid 42, with periods of non-agitated soaking used as desired. After the sample 20 is removed from the absorbent probe 18, the probe 18 is removed for the container 40 and may be discarded. The mixture of sample 20 and reconstituting fluid 42 are then available for further processing (such as removing fluid 42 to concentrate sample 20), or further testing (such as HPLC or GC or mass spectrometry analysis).

Alternatively, the holder 14 can be manipulated by a user or by automated equipment so that the sampling end 12 is at or in the open end of container 40 with the absorbent probe 18 positioned in the reconstituting fluid 42. The container 40 and reconstituting fluid can then be agitated, or not, with the holder 14 being used to hold the sample 20 in the fluid 42 until a desired amount of the sample is transferred to the reconstituting fluid 42. The holder and its absorbent probe 18 can then be removed and discarded if insufficient sample 20 remains on the probe 18. The non-sampling end of the holder 14 (opposite the absorbent probe) is preferably dimensionally matched to a pipette tip. The body of the holder is also preferably designed to fit into collection plates for easy extraction, and configured to fit into a rack (pipette tip holding rack or otherwise) for ease of use. The use of pipettes and pipette tips for holders 14 allows automation of the various steps described herein, as the holders 14 can be configured to work with existing pipettor or pipetting robotic systems.

Referring to FIGS. 5-6, the absorbent probe 18 is held in a holder 14 comprising a pipette tip. The pipette tip 14 may be placed in a tray 32 adapted to hold a plurality of pipette tip holders 14 and the absorbent probe 18. The sheaths 26 are preferably placed on these pipette tip holders 14 when they are in the tray 32 to further guard against contamination, but that is optional. The holders 14 and sheaths 26 are placed into one of a plurality of holes or openings 34 in the tray 32, which openings are configured to hold the pipette tip holders. The holders 14 may have enlarged ends or removable protective caps 36 to help reduce potential contamination of the inside of the holder 14 and its attached probe 18. The tray 32 may in turn be placed in a shipping case 30, which is shown in these figures as comprising a rectangular box configured to hold the tray, with a foldable lid 38 to cover the caps 36 and secure the pipette tip holders 14 in the shipping case 30. Various other configurations of trays 32 and shipping case 30 can be used.

Referring to FIGS. 2A, 2B and 10, the preferred method places the absorbent probe 18 in contact with fluid, such as blood 22 on a living animal. In its broadest sense living animals include humans as well as other animals. That direct contact with blood while the blood is on the animal eliminates the need to collect blood in capillary tubes and transfer the blood to an absorbent material. Nonetheless, if the fluid 22 is located in a container, capillary tube or any other location, the absorbent probe 18 can be placed in contact with the fluid to transfer a sample 20 (FIG. 2B) of the fluid 22 to the absorbent probe.

Figure 7:
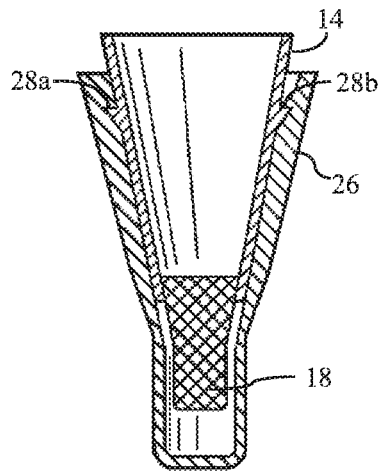
FIG. 7 is a sectional view of a holder containing an absorbent probe with a protective sheath connected to a hollow holder and covering only the probe and a portion of the adjacent end of the holder.
Figure 9:
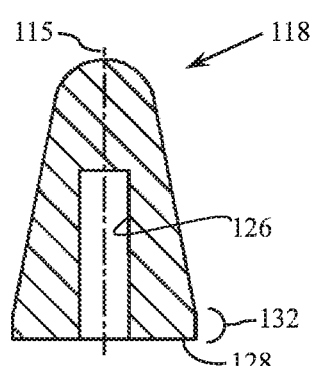
FIG. 9 is a cross sectional view of the probe of FIG. 8.

Referring further to FIGS. 7-9, the absorbent probes 18 can have various shapes but are preferably circular, rectangular, square or triangular in cross section orthogonal to the longitudinal axis 115. Short cylindrical shapes or frustaconical shapes are believed preferable for use with pipette holders 14, but the shape may vary to facilitate mounting to and/or removal from holder 14. The absorbent probes 18 are preferably made of a material that absorbs a predetermined volume of sample 20 from a larger fluid source 22, regardless of the time the absorbent probe is in contact with the fluid source—at least over a short period of time measured in several seconds. The absorbent probe 18 thus has a dynamic response range measured in seconds rather than fractions of a second. Rods made of a porous, hydrophilic polymeric material are believed suitable, with hydrophilic polyolefin being preferred and hydrophilic polyester being believed suitable but slower in absorption rates. If the polymeric material is not initially hydrophilic then there are numerous methods for converting the surfaces of the material (both external and internal) into a hydrophilic state. Methods for creating hydrophilic surfaces include adsorptive treatment with surfactants such as Tween-40 or Tween-80 to create hydrophilic surfaces. Tween 40 is made of polyoxyethylene (20) sorbitan monopalmilate. Treatment may also occur with other molecules containing both hydrophilic and hydrophobic elements. The hydrophobic elements will interact strongly with the hydrophobic polymeric probe material and expose the hydrophilic elements creating hydrophilic surfaces. Additionally treatment with plasma (Corona, Air, Flame, or Chemical) is another well-known method of adding polar groups to the surfaces of such materials, including oxygen plasma treatments. Likewise, the grafting of hydrophilic polymers to the surface and the chemical functionalization of active groups on the surface with polar or hydrophilic molecules such as sugars can be used to achieve a hydrophilic surface for probe 18. Covalent modification could also be used to add polar or hydrophilic functional groups to the surface of probe 18, 118. There thus numerous ways of achieving a polar or hydrophilic surface for the probes 18, 118

The material of probe 18 must be porous in order to absorb fluid. The internal volume of the absorbent probe material (pore volume) is preferred to be between about 30% and 50% of the total volume of the material. Additionally, the nature of the absorption requires small pores (preferably cylindrical tubes although irregular shapes are also sufficient) that are nominally 20-50 micron in diameter or largest cross-sectional dimension.

Hydrophilic polyolefin with a density of about 0.1 to 1 g/cc are believed suitable, with densities of about 0.2-0.7 g/cc preferred, and densities of about 0.5 to 0.7 g/cc being believed to be more preferable. A hydrophobic polyethylene with a non-porous density of about 0.92 g/cc which is fabricated as a porous material with a density of about 0.6 g/cc and is then plasma treated to make it hydrophilic is also believed suitable. The more easily manufactured absorbent materials are believed to have a density of about 0.4 to 0.8 g/cc. As the density increases the time to absorb fluid sample 20 increases. For blood absorption a shorter time is believed preferable when the sample 40 is taken from a live subject providing a live source of fluid 22, as by contacting the probe 18 with a cut 23 in a person's finger. Absorption times of about two seconds are believed suitable for blood from a live subject. The times will vary with the volume of fluid sample 20 desired and its source fluid 22. Materials other than polyolefin may be used, including sintered plastics which may provide more rigidity but maintain the high absorbance rate.

The density affects the time for the dried fluid sample 20 to be reconstituted. Blood absorbed by the lower density material reconstitutes faster than does the higher density material. About 88% of the blood absorbed by hydrophilic polyolefin having a density of about 0.18 g/cc was recovered in about five minutes using vortex, with the vortexing followed by two hours of non-agitated soaking providing slight additional gains up to about 90%. If denser materials are used on the absorbent probe 18, the reconstitution times will increase if over 90% of the sample 20 is to be recovered. Reconstitute times from 5-20 minutes, with agitation or vortexing, combined with non-agitated soaking, are believed suitable to recover suitable amounts of the dried sample 20 from the absorbent probe 18.

As the contacting area of the hydrophilic probe 18 increases the time to absorb the fluid sample 20 decreases. Thus, for faster absorption larger contacting areas are used on the absorbent probe 18. But a larger area on probe 18 does not maximize the absorption rate if the area of the fluid source 18 is much smaller than the contacting area of the absorbent probe 18. Thus, the anticipated size of the source 18 is advantageously considered in configuring the absorbent probe 18. A cylindrical probe 18 with a diameter (or other shape having a size providing an equivalent area) of about 2-6 mm is believed suitable for use with blood, with diameters of about 3-4 mm being preferred for samples of about 10-14 mg of blood, absorbed in about two seconds, for the most preferred polyolefin with the most preferred density. A probe length of about 1-5 mm is believed suitable when the sample 20 and fluid 22 are blood, with lengths of about 2-3 mm being preferred. Areas of about 6-20 mm$^2$ are believed especially suitable for the tip of the absorbent probe 18 when the fluid source 22 comprises blood formed by a finger prick, with areas of about 10 mm$^2$ being believed even more suitable. Shapes that maximize surface area of the contacting portion of the absorbent probe 18 while reducing dripping are believed desirable. Flat ended cylinders or semicircular ends on cylindrical probes 18 are believed desirable, but various configurations can be used.

The volume of the absorbent probe 18 is selected to absorb a predetermined volume of sample 20 from source 22. When the sample 20 is blood, a sample volume of about 18-21 µL is believed suitable, and absorbent probes 18 about 3 mm-3.5 mm in diameter and about 2 mm long, with a density of about 0.1 to 1.3 g/cc are believed suitable for absorbing that volume of blood in about two seconds. Similarly, probes 18 about 4 mm long absorbing a volume of about 8-12 µl, and preferably about 10 µl, in 2-4 seconds are believed desirable. For these probes, it takes about two hours at ambient room temperature to dry the sample 20 absorbed into the absorbent probe 18.

The device 10 is manufactured under sterile or aseptic conditions in accordance with international safety standards for direct subject sampling. Alternatively, the device 10 may be terminally sterilized after manufacture and before packaging. The device 10 is preferably a single use device to be discarded after the absorbent probe 18 is used once.

While the sample 20 is preferably dried, the absorbent probe 18 may be covered by suitable protective sheath 26 (FIG. 7, 13) or placed in a sealed container so the device can be transported to a location for analysis. Shipping wet biological fluids requires special steps, but it can be done.

Figure 14A:
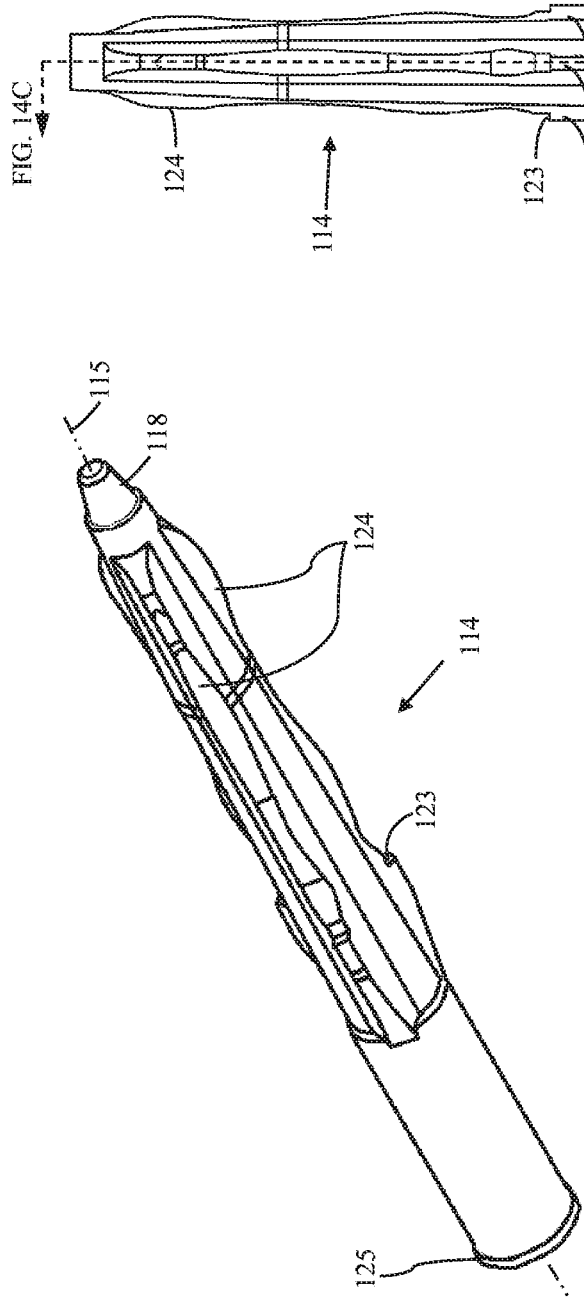
FIG. 14A is a top perspective view of a further embodiment of a holder and probe.
Figure 14B:
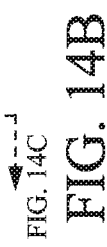
FIG. 14B is a top elevation view of the holder of FIG. 14A.

Referring to FIGS. 8, 13 and 14, various configurations of holders 114 are shown. In FIGS. 8 and 13, the holder 114 has a projection onto which the probe 118 is mounted and in FIG. 14, holder 114 has a tubular holder with an opening into which the probe 118 fits. Except for the way the absorbent probe 118 is held the holders are generally the same. Referring first to FIGS. 8 and 13, the holder 114 extends along a longitudinal axis 115, having a larger diameter open end 116 sized to fit over and nest with a pipette tip, and a smaller diameter tip that is closed. Advantageously, the tip has a post 120 extending therefrom. This embodiment has no circular flanges extending perpendicular to the longitudinal axis 115. The flange 123 (FIG. 8) adjacent probe 118 is preferably omitted in this embodiment to avoid retaining any fluid on the flange during extraction. A plurality of longitudinal ribs 124 extend along a portion of the holder length and preferably extend between adjacent flanges. Advantageously 3-4 ribs 124 are used, equally spaced around the outside of the holder 114, to allow easy gripping and manipulation by a person's fingers. The ribs extend along the length of the holder along axis 115, between the manipulating end and the probe end of the holder. In the illustrated embodiment of FIG. 8, the ribs 124 curve inward toward the holder 114 between the flanges 124 to better conform to the tips of a person's fingers, while the ribs 124 in FIG. 1 have a different curvature. A holder about 2-4 inches long, with flanges 122 spaced about every one or two inches is believed suitable. The ribs 124 may serve several functions in addition to making it easier to grip and manipulate the device 10. The ribs 124 may help align the device 10 with the portions of case 30 configured to receive each device 10. The case 30 may have recesses configured to receive one or more ribs 124, or an opening in the case may have recesses configured to receive one or more ribs and guide the rib into position within the case. The ribs 124 may also hold or position probe 18, 118 in spaced relation to the adjacent wall of case 30. The ribs 124 may also be configured to allow a robotic handler grab and position the device 10 and its associated probe 18, 118.

Referring to FIGS. 8-9, the post is advantageously cylindrical in shape and extends along longitudinal axis 115. The absorbent probe 118 has a cavity 126 shaped to conform to the post 120, and preferably slightly smaller so the probe 118 resiliently grips the post 120 to hold the probe on the post. An optional adhesive could be used as desired to further hold the probe and post together. The probe resembles a truncated cone with a wider diameter base 128 and a narrower diameter distal end 130 that is preferably rounded. The base end 128 may have a cylindrical section 132 of uniform diameter before tapering toward the distal end 130. The cavity 126 extends about ⅔ the length of absorbent probe 118 measured along the axis 115. The interior end of cavity 126 forms thick sidewalls on the absorbent probe 118. The sidewall thickness increases toward the base 132 and the distance from the end of cavity 126 to the outermost portion of distal end 130 along axis 115 is preferably two or more times greater than the thickness of the sidewalls. Advantageously, the probe 118 is configured so the distal end 130 rapidly absorbs blood, and rapidly wicks the blood throughout the body of the absorbent probe 118.

The absorbent probe 118 is made of hydrophilic porous material with a controlled porous volume. A hydrophilic polymer with a pore volume of about 40% is currently available and believed suitable. An internal standard may optionally be pre-adsorbed onto the probe 118 and dried. The probe 118 and holder 114 are placed in sterile or aseptic packaging and provided to the user in single units or packages of plural units, such as four as shown in FIG. 11, or three shown and described later.

Referring to FIGS. 2 and 10, the holder 114 is held by hand and a user places the absorbent probe 118 in contact with blood, as for example, arising from a finger prick. The probe 118 could be placed in contact with the blood various ways, including immersing in a sample in a container, swabbing a cut, contact with a pool of blood, or other means. The blood is absorbed by the probe 118 in the timelines discussed herein. Advantageously, the probe 118 is sized and configured to absorb a predetermined volume of blood in a predetermined amount of time, such as 10-15 ul in about 1-4 seconds and preferably less.

Figure 11:
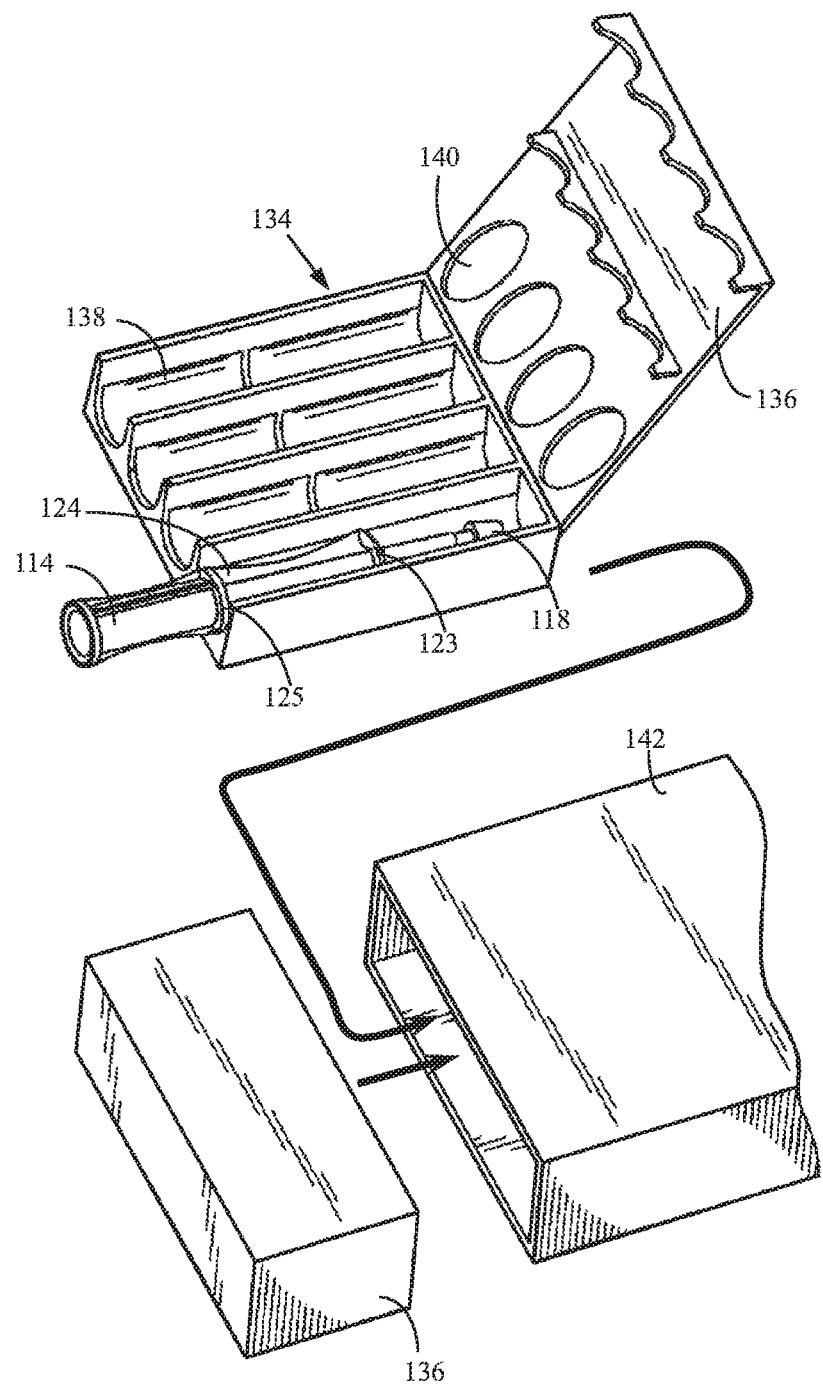
FIG. 11 is an exploded perspective view showing the holder of FIG. 8 in a shipping container having separate compartments for each of a plurality of holders and the probes associated with the holders.

Referring to FIG. 11, the holder 114 may be placed in a container 134 having removable lid 136 and one or more racks or compartments 138 or racks configured to receive one or more holders 114. Advantageously, the compartments 138 may comprise tubular compartments, preferably cylindrical compartments, having an inner diameter slightly larger than the diameter of flange 122 and slightly smaller than flange 123 so flange 123 abuts a wall on the container 134 to limit the distance the holder 114 is inserted into container 134. The flange 123 and adjacent walls of tubular compartment 138 help restrain the holder 114 from moving laterally. Air holes 140 in the walls of container 134 may be provided to allow air to circulate through the container 134 at the location of the absorbent probe 118 and are preferably large enough to sufficient to dry the probe in 2-3 hours in an ambient laboratory room temperature and humidity. The illustrated embodiment places circular holes in opposing walls of the container 134 located at the absorbent probe 118 so air can pass through the container at the location of the probes to dry them. A bottom portion 142 of the container may fit on the upper portion 136 to cover the holes for shipping. Lid 134 is placed on the top of the container 134 and configured to provide a wall close to or abutting the flange 125 so the holders 114 don't move much during shipping. Instead of or in addition to the flange 125, the ribs 124 may extend along a sufficient length of the holder 114 and fit close enough to the walls of the recess 154 in the well plate or container 150 (FIG. 12) so as to position the probe 18, 118 relative to the recess in which the probe is placed. As desired, a foam material or other resilient material may be provided to abut portions of the holder 114 and hold it in position during shipping. A surface on container 134, lid 136 or bottom 142 is preferably provided for adding information on the holders 114 and probes 118, such as the name or identification number of the person associated with the blood on a particular probe 118. Thus, a user can grab the end of a holder 114, absorb a blood sample on probe 118, place the holder and absorbed sample in container 134 and allow the sample to dry. When dried, the lid and bottom can be put on the container 134 for shipping.

Referring to FIGS. 15-18, a further transporting or shipping container 164 is shown having a removable top 166 and bottom 168 portions releasably held together by an optional snap lock 170a, 170b on at least one and preferably on two opposing sides of the container 164. The top 166 could be hinged, but separable parts are preferred. The top 166 is preferably rectangular in cross-section with an exterior top that is flat and may rest securely on a flat surface such as a table during use. The top 166 has a plurality of recesses 172 (FIG. 16), preferably cylindrical, configured to receive the end of holder 114 during use of the container and having an end wall 173. Three recesses 172 are preferred, but the number can vary. A mounting projection 174 extends from the center of each recess 172. Each mounting projection 174 advantageously has a number of ribs 176 extending outward from the projection and along a length of the projection. A hole 175 extends through the end wall 173 between each rib so air can circulate through the holes or openings 175. Advantageously there are several air-flow openings 175. As best seen in FIG. 16A, the bottom of the circular recess 172 is slightly conical so it inclines slightly inward toward the mounting projection 174 and the mounting projections are slightly conical so the bottom of the mounting projection 174 tapers slightly tapered outward. The manipulating end of holder 114 with the (optional) flange 125 fits between these two tapered portions.

Figure 18A:
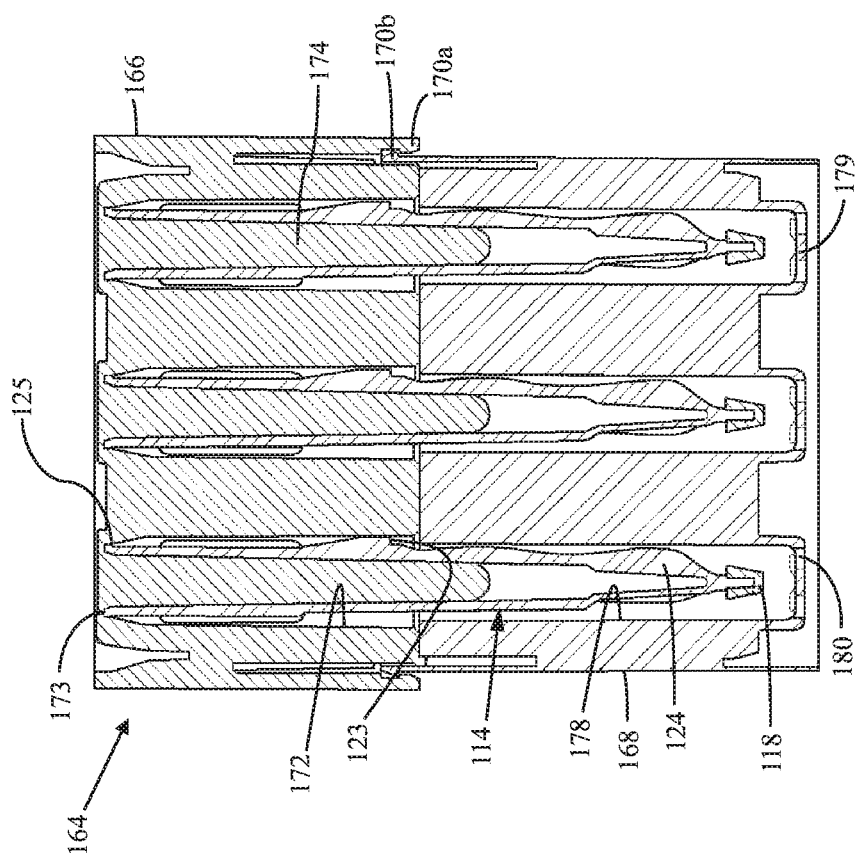
FIG. 18A is a sectional view of the container of FIG. 15A with holders therein, taken along 18A-18A of FIG. 18B.

As best seen in FIG. 18A, the manipulating end of holder 114 adjacent the flange 125 (FIG. 13) is hollow and that end and the ribs 176 are sized to nest together so the holder 114 fits over the mounting projection 174 with a slight interference fit. Advantageously, the holder 114 has a slightly tapered, internal, conical passage that mates with a slightly conical exterior shape on mounting projection 174 and its ribs 176 so the two parts wedge together with the ribs 176 abutting the inside of the manipulating end of holder 114. If desired, the outer diameter of the end of the holder 114 may abut the walls of the recess 172 at the tapered bottom of that recess in order to form a slight interference fit, but that is not believed necessary.

The holder 114 and container parts 166, 168 are preferably made of molded plastic and given the molding tolerances sight interference fits between the holder 114 and one or both of the mounting projection 174 or recess 172 are possible. The end wall 173 may abut the end of the holder 114 or the end flange 125 on the holder 114 to limit the maximum relative motion between the mounting projection 174 and the manipulating end of holder 114. The length of projection 174 is long enough to ensure alignment of the holder 114 releasably fastened to that projection. The projections 174 are parallel, and coincide with longitudinal axis 115 of the holders and the axis of a recess 173 in the bottom 168 during shipment or transportation of the holders.

Figure 18B:
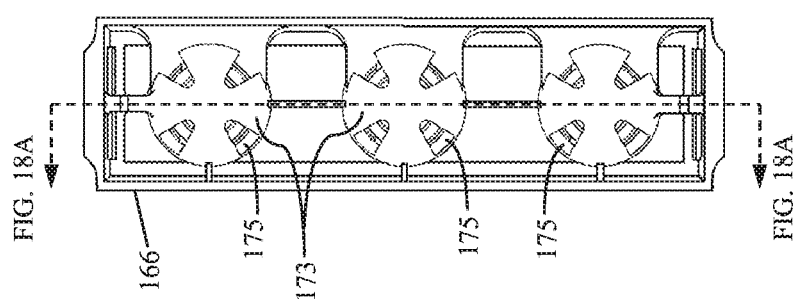
FIG. 18B is a top elevation view of the container of FIG. 18A.
Figure 18C:
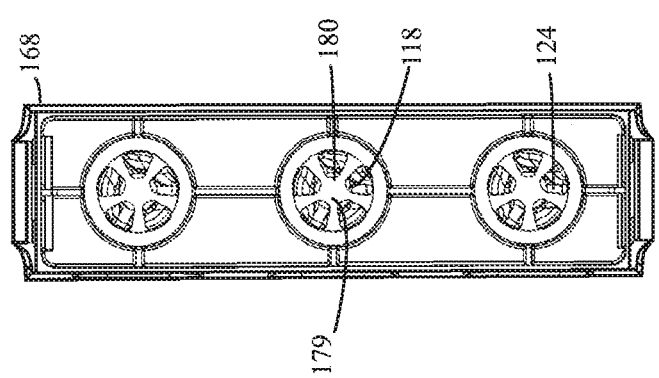
FIG. 18C is a bottom elevation view of the container of FIG. 18A.

Referring to FIGS. 15, 17 and 18, the bottom portion 168 of the container 164 has recesses 178 (FIGS. 17E, 17B), each with a bottom 179. The recesses 178 are located to match with the recesses 172 in the top 166 to form compartments within which the holders 114 and probes 118 are releasably held for transportation. The recesses 172, 178 in the top and bottom portions 166, 168, respectively, are preferably cylindrical recesses to form cylindrical compartments. The bottom 179 has air openings 180. Five openings 180 are shown but the number may vary. As best seen in FIG. 18A, the holder 114 has ribs 124 sized to fit inside the recesses 178, preferably with a small clearance between the outermost portion of ribs 124 and the adjacent walls forming cylindrical recesses 178. The ribs 128 and recesses 178 cooperate to keep the probe 18, 118 from hitting the walls forming the recesses 178.

The end of the holder 114 adjacent flange 125, or the flange 125 on the manipulating end of holder 114 abuts the closed end 173 of the wall forming the recess 178 to limit movement of the holder 114 relative to the recess 172 and top portion 166 of the container 164. That occurs when the holder 114 is wedged onto the mounting projection 174 with a slight interference fit. The holders may be pushed off of the mounting projection 174 by inserting prongs or fingers through openings 175 in the bottoms 173 of recesses 172. If the holders 114 are not wedged onto projections 174 then if the top 166 is vertically above the bottom 168 the holders 114 will fall toward the end 179 of the recess 178. The notches 123 in the ribs 124 or a similarly located flange or other projection on holder 114 will abut the open edge forming recess 178 to limit the relative position of the holder and its probe 118 within the recess 178. Thus, the tubular compartment formed by aligned cylindrical recesses 172, 178 contain the holder 114 and its associated probe 118, with the shape of the holder 114 and mounting projection 174 limiting movement within the top portion 166 of the container 164, and with the notch 123 on the holder 114 and the ribs 124 limiting movement within the bottom portion 168 of the container.

In use, the lid or top 166 of the container 164 has a holder 114 inserted into each recess 172 of the top 166 and preferably held by a slight interference fit with the recess or the mounting projection 174. The mounting projections 174 and holders 114 are removably held together by a slight interference fit so manipulation of the top 166 moves and positions all three holders together. The top and bottom portions 166, 168 are then placed together with the holders 114 fitting into the recesses 178 of the container 164. The centerline of the recesses 172, 178 coincide with centerline 115 of the holder 114. The recesses 172, 178 join to form compartments and within each compartment a holder 114 and its associated probe 118 are held. Air can flow through openings 175, 179 to dry the absorbent probe 18, 118 on the holder 114 held within the container 164. The ribs 124 extend sufficiently along the length of the holder 114 so that they position the holder inside the recess 178 and help avoid the probe 118 hitting the sides of the compartment that includes recess 178. The snap lock portions 170a, 170b on top 166 and bottom 168 engage to releasably hold the top and bottom portions of container 164 together.

Advantageously, under aseptic conditions the holders 114 (with their probes 118) are initially placed by machines (e.g., robotic manipulators) onto the mounting protrusions 174. A slight interference fit is used to securely but removably fasten the holders 114 to the protrusions 174. The top (with holders 114) and bottom portions 166, 168 are then fit together manually or by machines, such as robot manipulators. Thereafter, a series of ejectors, one for each recess 172, and having one or more fingers aligned with the openings 175, are passed through the openings 175 to push the holder 114 off of the mounting projection 174 so the flange 125 abuts the top of the wall forming recess 178 in the bottom portion 168. This is done under aseptic conditions. If any chemicals are to be added to the absorbent probe 114, such as a surfactant, reference standard, anticoagulant, stabilizer (e.g., inhibitor enzymes), modifier (e.g., Betaglucuronidase), etc., it is preferably added before the holder 114 is positioned on the mounting protrusion, but could be added before the top and bottom portions 166, 168 are fit together. Such chemical addition is preferably done under aseptic conditions. The assembled container 164 with holders 114 in each compartment may then be placed in a sterile bag for shipment to the user. The bag is optional.

In use, a user unfastens the releasable lock 170 and removes the top portion 166 of container 164. Since the manipulating end of the holder 114 was pushed out of interfering engagement with the mounting projection 174 the lid or top 166 may be readily removed without removing the holders 114. The user may remove each holder 114 separately to directly acquire a sample using the probe 18, 118. Since the manipulating end of the holder 114 was pushed out of interfering engagement with the mounting projection 174 the holders rest in the bottom portion 168 of the container by gravity and may be easily removed by the user with one hand. After sampling, the holder 114 and probe may be placed in a drying rack, or advantageously placed back in the recess 178 of the container 164. A portion of the holder 114 abuts the container 164 to position the absorbent probe 18, 118 adjacent to, but not in contact with, the bottom 179 and its air openings 180. The abutting portion or positioning limit may be flange 125 (FIG. 18A), or it may be a notch 123 in one of the ribs 124 (FIG. 18A), or it may be another surface on the outer surface of the holder 114. Three holders 114 are preferred in order provide one sample for analysis, one as a backup if the initial test goes wrong, and one may be used for future verification or retesting. But different combinations of holders may be provided in kits or containers of various quantities.

Figure 19:
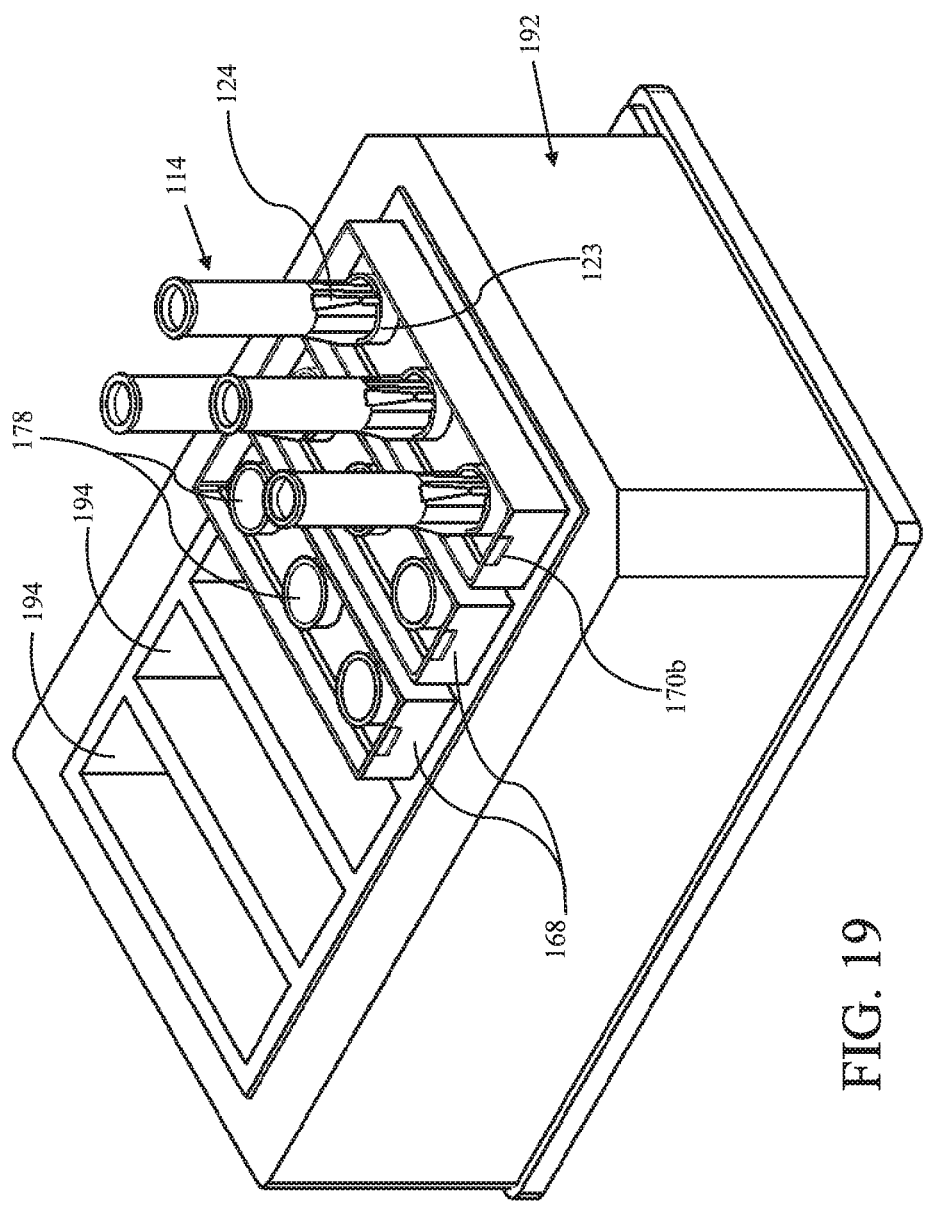
FIG. 19 is a perspective view of a case with a plurality of containers and holders therein.

Referring to FIGS. 19-20, for large scale sampling operations it may be desirable to have a plurality of containers 164 and their holders 114 available. A base 192 may be provided with a plurality of recesses 194 configured to receive the bottom portion 168 of the container 164. This base 192 may be used during sampling, or after sampling at the processing laboratory, or for drying. If used for drying, the base 192 may be heated, as for example, by heating coils in the bottom of the base or sidewalls of recess 194 adjacent absorbent probes 118. The base 192 and containers 164 are advantageously configured to locate the holders at predetermined locations suitable for robotic manipulation. Spacing the centerlines of the holders 114 at about 18 mm apart is believed suitable for this purpose.

A series of common numbers, letters etc. are applied to the container 164 and each holder 114 within the container to identify them as corresponding to the same subject or patient and make it easier to coordinate results if individual holders 114 become separated during sampling or analysis. As seen best in FIGS. 15A, 15B, 16C and 16F, the top 166 of the container 164 has an access port 182 on at least one side of the top 166, with one access port aligned with each recess 172. Rectangular shaped access ports 182 are shown, but the shape can vary. The access ports 182 are sized and configured to allow visible indicia to be applied to the holders through the ports 182.

When the holders 114 are held on the mounting probes 174 and the top and bottom portions 166, 168 of the container 164 are assembled to enclose the holders and probes 18, 118, the access port 182 allows access to the outside of the holder through the port. Thus, when the holders 114 and probes 18, 118 are packaged for shipment in container 164, identifying indicia 181 (FIGS. 13A, 15A, 15B) can be affixed to each holder 114 and to the container 164 or top 166. The identification indicia is advantageously a serial number associating each holder 114 in the container 164 with the other holders in the container 164 and with that container. While printed indicia printed on the holder 114 is preferred for indicia 181, adhesive labels are also believed suitable as are other mechanisms for providing visible indicia to the holders. Advantageously, the ribs 124 on the holder 114 do not extend to the end of the holder adjacent flange 125 which is opposite the probe 18, 118 and thus the end of the holder has a generally smooth and preferably cylindrical outer surface which can readily accommodate printed indicia or labels 181 as applied through access ports 182. The access ports 182 thus extend along a sufficient length of the top 166 to allow the visible indicia to be applied through each port to the holder 114 aligned with or corresponding to each access port. The access port 182 allows air passage into the recess 172, 173 of the container 164 and helps dry the absorbent probes 18, 118 when the container is closed. The bottom part 168 of the container preferably does not have any openings, but could have some if it believed desirable, for example, for drying of probes 118.

As best seen in FIGS. 16C and 16F, the top 166 has a recessed portion extending around its periphery to form an offset male projection 184. The bottom 168 has a correspondingly configured recess 186 (FIGS. 17B, 17F) on its inner periphery shaped to mate with the projection 184 in the top 166 to better hold those parts together. The male and female mating projection 184 and recess 186 could be on the opposite parts. On an outward facing portion of the inset, male projection 184 there are preferably visible indicia 188 which identify the recesses 172 and holders 114 therein. The indicia 188 preferably comprise numbers such as numerals 1, 2 and 3, or letters or other simple designations associated with a different one of the sequential recesses 172 and the corresponding mounting projections 174. The indicia 188 may be molded with the formation of the top 166, or it may be printed, or otherwise applied. The indicia 188 helps the user associate a specific holder 114 with its mounting projection 174 and recess 172. The indicia 188 on the top 166 is preferably associated with the visible indicia 181 on the holders 114 so a user can more easily remove a holder 114 from its associated recess 172 and mounting projection 174, use its associated probe 18, 118 and then return the holder to the same recess 172 and mounting projection 174. Advantageously, a portion or all of indicia 181 is contained in indicia 188, or vice versa.

By pushing the holder down into the recess 172 and along the length of the mounting projection 174 the user can wedge the holder in place on the top 166, preferably by an interference fit with the ribs 176 on mounting projection 174, but alternatively by an interference fit with the walls forming recess 172 in the top 166. Wedging the holder 114 in place not only helps releasably fasten the holder to the top 166, bit it helps align the holder with projections 174 and that makes it easier to insert the holders into the bottom 168 of the container 164.

Figure 12:
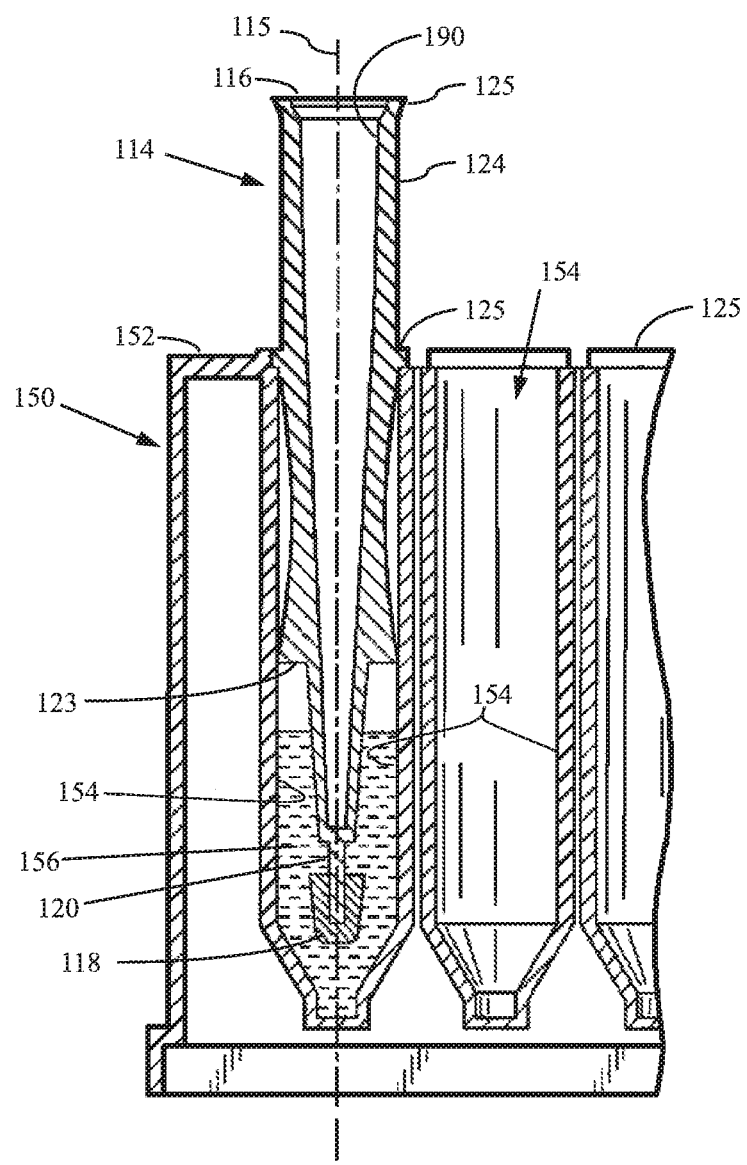
FIG. 12 is a cross sectional view of a portion of a well plate having the holder of FIG. 8 therein, along with an extraction fluid.

Referring to FIGS. 12 and 20A-20B, when container 134, 164 is received at a laboratory or processing location, the holder 114 and associated absorbent probe 118 are removed from the container and placed in a well plate 150 by manually or robotically grabbing the end of the holder opposite the probe 118 or by inserting pipette handling equipment into the open end of the holder, or by robotic handling equipment. The well plate 150 conforms to SBS Microwell plate specifications and has a top wall 152 with plurality of tubular recesses 154 opening onto that top wall. The recesses 154 are typically cylindrical in shape, often with tapered, closed ends. Advantageously the flange 125 or notch 123 on holder 114 is sized so that it abuts the top wall 152 to position the absorbent probe 118 adjacent the bottom of the recesses 154, with flange 123 and ribs 124 being sized relative to the diameter of recess 154 to limit lateral motion of the holder 114 in the recess. Thus, the holder 114 is inserted into a recess 154 of the well plate 150. The length of the holder 114 and the location of the flange or notch 123 may be selected to position the absorbent probe 118 at a desired position within the recess 154 of well plate 150. The flange 123 may be omitted in which event the ribs 124 cooperate with the walls forming recesses 154 to keep the dried absorbent probe 118 centered in the recess and away from the recess walls during processing. Instead of a well plate 150, the holder 114 and probe 118 could be placed in a single tubular container.

Once the holder 114 and absorbent probe 118 are positioned in the recess 154 of well plate 150, suitable extraction fluids 156 are added to the recess 154. The fluids 156 may be in the recess 154 before the holder and probe are placed in the recess. Typically, the well plate will be vortexed, sonicated or otherwise agitated to intermix the fluids 156 and (dried) blood on the probe 118 to extract the blood from the probe. If a flange 123 (FIG. 8) is used on the holder 114 the flange can act as a cap and/or splash guard during extraction vortexing, sonnication or agitation. Since vortexing may cause the solvent to climb the walls of recess 154 the flange 122 may optionally be provided above the maximum height of the vortexed fluid in order to avoid the back side of the flange from collecting the intermixed fluids and impeding complete recovery of the sample. Alternatively, the flange 123 may be placed close enough to the wall of the recess 154 to disrupt vortexed fluid from climbing the wall.

Alternatively, the holder 114 may have the ribs 124 extend toward the probe 118 a distance sufficient so that the ends of the ribs are within the vortex cone of extraction fluid 156 formed during vortexing so as to disrupt the vortexed fluid from climbing the walls of the recess 154. Advantageously, the end of ribs 124 are sized to be spaced slightly apart from the wall of recess 154 so as to help position the probe 18, 118, but close enough to the wall of recess 154 to disrupt the vortex and cause more extraction fluid 156 to engage the probe rather than clime the wall of the recess due to spinning. A clearance of about 0.001 inches (about 0.03 mm) on between the outer periphery of the ribs and adjacent walls of the recess 154 is believed suitable.

After the dried blood or other sample fluid on probe 118 is extracted by extraction fluid 156, the fluid is removed by various means through the top or bottom of recess 154. The holder 114 and probe 118 are typically removed from the well plate 150 and recess 154 to allow access to the fluid therein for easier removal of the fluid, or in some instances for further processing of the fluid within the recesses 154. The holder and probe may then be discarded, or retained according to specific needs. The fluid 156 with the sample extracted from absorbent probe 118 is then further processed to further analyze the sample.

This above method and apparatus are especially useful for testing of biological fluids, especially for sampling blood for use in testing for either research or for diagnostic use. The fluid sampled does not have to be free of or separated from red blood cells (plasma or serum). Indeed, the absorbent probe 18, 118 is preferably used to absorb fluid directly from the sample, and is believed particularly useful for absorbing whole blood from a pricked finger. Thus, the probe 18, 118 advantageously absorbs both the liquid portion of blood (plasma) as well as the red blood cells.

The probe 18, 118 is used to directly contact the source of fluid to be sampled. This differs from prior art devices that used capillaries or narrow filtering passages to contact a fluid source and connect to a fluid retaining matrix or cavity. By directly contacting the fluid source with the sorbent probe 18, 118 the uptake or absorption of fluid is increased and the time to do so is reduced. Thus, advantageously a majority (over 50%) of the surface area of the absorbent probe 18, 118 is exposed and available for both absorbing fluid and allowing access to air and gasses to dry previously absorbed fluid. The material selected for the probe 18, 118 is thus both fluid permeable to increase absorption rates, but also gas permeable to increase drying rates and shorten drying times. Preferably, a substantial majority (over 80% and preferably over 90%) of the surface of probe 18, 118 is available for contact with the source of fluid and available for drying absorbed fluid. By having such a large surface area available for absorption and drying, the ease of manipulating the absorbent probe 118, positioning the probe relative to the fluid 22, and the ease of contacting the fluid with the probe are all greatly increased. The large portion of exposed surface also helps shorten the drying time.

Referring to FIG. 9, the probe has a length L extending along a first, longitudinal axis 115, and sides surrounding that axis with the sides being of various shapes, including curves, planes or combinations thereof and being of various number. Preferably the shape is selected or the probe configured so the absorbed fluid 22 travels about the same distance into the probe regardless of where the fluid contacts the surface of the probe 18, 118. Thus, the exterior surfaces of probe 18, 118 orthogonal to the longitudinal axis L are preferably about the same, say within about 20% of the axis 115.

Figure 14C:
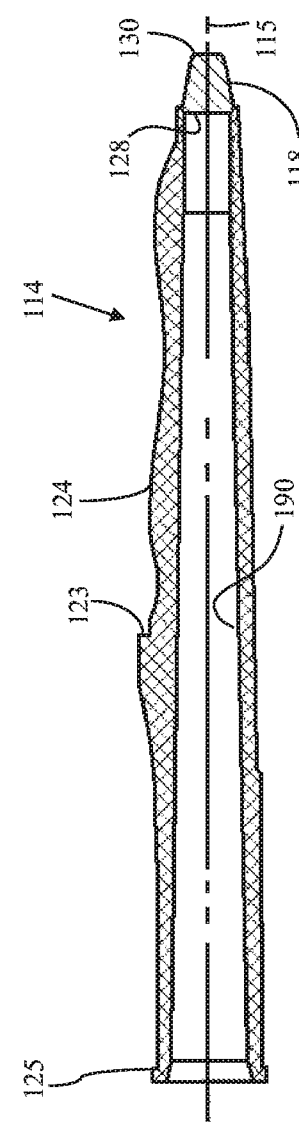
FIG. 14C is a sectional view of the holder and probe of FIG. 14A, taken along section 14C-14C of FIG. 15A is a top perspective view of a container for three holders.

Referring to FIG. 14C, the holder 114 is preferably tubular adjacent the end of the holder opposite the probe 118. The recess 190 forming the tubular shape may extend entirely through to the holder 114. That construction allows solvent to be poured into the recess 120 and pass from inside the holder through the probe 118 and out the outer surface of the probe in order to remove previously absorbed and dried fluid 22 from the probe. A passageway with a circular cross-section that is constant, or preferably that tapers slightly along the length L of the holder 114 is believed preferable. In the configuration of FIG. 14C, the outer periphery of the probe 118 is placed in the opening at the end of the passageway or recess 190 and preferably press fit into position to block the opening and hold the absorbent probe 118. Alternatively, suitable adhesives may connect the parts, or mechanical fastening means such as small hooks or deformations of the holder 114 that extend inward toward axis 115 and are located around the opening in the probe-end of the holder 114 could be used to create an interference fit between the tubular tip of the holder and the abutting periphery of the probe 118.

As seen best in FIGS. 12, 13B, 14C and 18A, the absorbent probe 18, 118 has an exterior surface that is preferably fully exposed so that except for the connection to the holder 14, 114 the surface of the probe is exposed and available for contacting with the fluid to be sampled. It is believed to make the probe 18, 118 elongated with a connection to holder 4, 114 at one end of the probe. Advantageously, the connection of the probe 18, 118 to the holder 4 is such that less than about 25% and preferably less than about 15% and more preferably less than about 10% of the surface area is blocked by the connection and not exposed for directly contacting the fluid to be absorbed. Likewise, the surface of the absorbent probe 118 is not sheathed or shielded by any material that would prevent absorption of fluid 22 during use, or that would impede access of air or other gas to dry the fluid absorbed by absorbent probe 114.

The material used for the absorbent probe 18, 118 should be hydrophilic. The material may initially be hydrophobic or hydrophilic and treated to make it hydrophilic. Hydrophobic matrices may be rendered hydrophilic by a variety of known methods. Among those methods available are plasma treatment or surfactant treatment of the matrix. Preferably, plasma treatment is used to render a hydrophobic material such as polyolefin, preferably polyethylene, and make the material hydrophilic. Further, given the above disclosure it is believed that one skilled in the art would understand that there are a variety of plasma treatments or other processes to impart hydrophilic character to an otherwise hydrophobic the probe material and to create a stable material whether that material be hydrophobic or hydrophilic to begin with.

Surfactant treatment involves dipping the hydrophobic matrix in a surfactant and letting it dry. This surfactant treatment assists in wetting the surface and interior of the matrix and results in the promotion of aqueous liquid flow through the matrix. It is contemplated that a wide variety of commercially available surfactant materials would be appropriate for use with the present invention. The surfactant treatment has the disadvantage of potentially adversely affecting later processing of the sorbent 18, 118 and fluids retained therein, depending on the particular analyte, solvents and analysis involved. The surfactant is thus preferably chemically stable relative to the fluid being sampled. If that fluid is blood, the treatment of such hydrophilic material to make it chemically stable (e.g., by pre-adsorbing a surfactant such as Triton X) can lead to interference in the analysis of the sampled or absorbed fluid, so the specific surfactant used may limit the use of the probes 18, 118. Note that surfactants are preferably adsorbed onto surfaces of the probe rather than absorbed into the probe.

In general, surfactants should be selected which are compatible with the reactants or reagents placed within the matrix so as not to interfere with the preferred activity. Additionally, it should be noted that no surfactant should be present in such concentrations as to cause hemolysis of the red blood cells. In addition, care must be exercised to avoid hemodilution of the plasma sample. Hemodilution is the extraction into the plasma of the internal fluid of the red blood cell due to hypertonic conditions.

The material used for probe 18, 118 advantageously has a predetermined porosity and void space. The porous materials will retain fluid in their interstices in proportion to the volume of the porous matrix. Suitable materials for the probe 18, 118 include sintered glass, sintered steel, sintered ceramics, and sintered polymers of plastic, with the sintered polyethylene believed to be especially useful. Sintered polyethylene with a pore size of from about 10 microns to about 80 microns is believed especially useful. Such a pore size allows individual red blood cells to pass readily into the probe material. If the pore sizes are too small, then the time to absorb a predetermined sample volume will increase. The material and its porosity and pore size must be reproducible in order to provide a reproducible fluid uptake capacity of the probe 18, 118.

The treatment of the material used for the probe 18, 118 can also impart an ionic character to the probe material (or probe) which could be advantageous in selective adsorption and enrichment of analyte molecules. This added ionic character could be positive or negative charge, or specific chemical moieties such as phenyl, hydroxyl, or other groups that are believed to improve selectivity or retention for the analyte molecule(s) used in blood analysis and testing.

The probe 18, 118 could also be manufactured to entrap chromatographic particles with various desired chemical properties in order to allow for selective retention or enrichment of the analyte(s). The chromatographic particles would be added to the mold when manufacturing the probe in a desired concentration and be entrapped within the porous network of the probe material, in this case—sintered porous plastic The volume of the probe 18, 118 is advantageously kept small, just large enough to absorb about 30 microliters of a fluid sample 20, advantageously just large enough to absorb about 20 microliters of fluid sample 20, and preferably large enough to absorb about 10 microliters. Devices 10 sized accordingly are believed preferable, with a multi-volume device 10 having a probe 18, 118 sized to absorb about 5-20 microliters being believed desirable for multipurpose use. By keeping the probe 18, 118 and absorbed sample 20 small, several advantages can be achieved.

First, the absorption time is short since the volume to be absorbed is small and since the material of probe 18, 118 is selected to absorb fluid rapidly. The absorption is further increased when the majority (over 50%) or substantial majority (over 80%) of the entire surface of the probe 18, 118 is exposed for potential contact with the fluid sample 20.

Second, the small volume of the absorbed fluid sample 20 allows the sample to dry faster. Since biological samples degrade analytes, and since dehydrating the sample and analyte retards degradation, fast drying helps slow down the sample degradation. For example, if the desired analyte is a specific drug, enzymes in blood may degrade one or more drugs or analytes sought to be detected by testing. Drying the blood quickly helps slow down the degradation. Drying a small sample on probe 18, 118 are faster than drying a large sample. To reduce drying time, the material used for the probe 18, 118 is preferably selected to be air permeable or gas permeable so that air can enter the probe 18, 118 and dry it faster.

Third, dried biological samples are generally not classified as bio-hazardous materials and may be shipped through the mail, etc. That makes it easier for shipping and handling, and costs less than shipping fluid samples. A shortened drying time also allows more samples to be taken, dried, packaged and shipped per unit time, thus increasing efficiency and reducing costs. Fifth, small samples may be extracted faster from the probe 18, 118. Using devices 10 to allow and facilitate robotic handling also reduces time and costs of the analysis. Using probes 18, 118 configured for easy placement in analytical tubes, or having internal passageways for solvents to pass through the probes to extract the dried samples further reduces the extraction time. Sixth, the small probes 18, 118 leave less material for disposal. This is especially useful if the probes 18, 118 from which samples are extracted are still considered bio-hazardous materials. Seventh, the probes 18, 118 from which solvents have extracted the sample, may be dried more quickly, thereby making them more easily to handle, discard or destroy than wet absorbent materials.

The shape of the absorbent probe 18, 118 will vary and is preferably optimized to improve wicking speed. However the tip diameter of the probe need not be any larger than the diameter of a 30 ul spot of blood. A probe 18, 118 with a circular tip diameter of about 0.1 inches (0.25 mm) is believed suitable. A truncated, conical probe 18, 118 having a further length of about 0.16 inches (4 mm) and a base diameter of about 0.14 inches (about 3.5 mm) is believed suitable. The surface area of the probe in contact with the blood is preferably maximized and thus the sides and tip of the probe 18, 118 advantageously present an exterior surface area of about 59 mm (0.1 in$^2$). The area is preferably sufficient to contact the entire area occupied by a 30 microliter sample of blood on the surface on which the wound 23 is located producing the blood.

Additionally, the use of anticoagulants during the collection of blood may be useful in maintaining the homogeneity of the blood as well as preventing unwanted degradation. The addition of dried anticoagulants to the probe 18, 118 may help prevent these unwanted effects, An anticoagulant may be applied dry to the probe 18, 118 but is preferably applied wet or in liquid form and allowed to dry before use. Any anticoagulant applied to the probe 18, 118 is preferably selected for use with any anticoagulants in the matrix of any reference standards that are used, and is selected to be compatible with any fluids used in extracting the analytes from the dried blood or sample on the probe 18, 118. The most common anticoagulants fall into two categories polyanions (e.g. Heparin) or metal chelators (e.g. EDTA, citrate). Suitable anticoagulants are believed to include acid citrate dextrose, citrate phosphate dextrose, citrate phosphate dextrose adenine, sodium citrate, K2 EDTA, K3 EDTA, sodium EDTA, lithium heparin, sodium heparin, potassium and oxylate. Any dried anticoagulant applied to probe 18, 118 should be suitably matched with the extraction fluids and downstream analysis so as not to adversely affect the accuracy of the analysis.

The use of internal and external standards during analysis is common practice and a reference standard (wet or dried) may be applied to the absorbent probe 18, 118 during manufacture or sampling of the fluid, or it may be added to the reconstituting fluid when the dried blood or other fluid is extracted from the absorbent probe 18, 118. Many nonvolatile materials which do not affect the analysis of the blood or fluid may be used as reference standards. Radiolabels, fluorescent labels, deuterated labels may be used. For example, during extraction of the probe an analyst may add a standard for the analyte of interest to the extraction solvent. For ease of use, standards can also be dried onto the surface of the probe prior to use or after a sample has been collected and dried onto the probe, thereby eliminating the need to add internal standards to the extraction solvent. Additionally, a set of probes 18, 118 may be made with reference standards of dried blood that are to be processed along with the collected standards in order to check the extraction and/or analytical processes or to provide a reference for the extraction and/or analysis.

Additional treatments of the absorbent probe 18, 118 may be useful for the analysis of specific types of biological molecules such as proteins and nucleic acids. For each analysis, improving the stability of the molecules to be analyzed or preparing the molecule for analysis during drying and storage can improve later analysis. As an example of stability improvements, in the case of protein and peptide analysis it is useful to deactivate other proteins such as proteases which chemically degrade both proteins and peptides. Mixtures of protease inhibitors (and inhibiting molecules such as Urea and Salts) can be dried onto the surface or interior of probe 18, 118 so that proteins and peptides are stabilized during drying and storage. Likewise, in the case of nucleic acid analysis it can be valuable dry additives such as salts, chelators, enzymes which degrade nucleases (such as proteinase K) to prevent the activity of molecules that degrade nucleic acids. In the case of drugs and small molecules they are commonly metabolized into Glucuronides during conjugation for excretion. In the example of urine analysis it can be useful for later analysis to incorporate Beta-glucuronidases enzymes into the probe 18, 118, which will convert the drug for analysis back into its original form.

Not only is the absorbent probe 18, 118 useful for fast absorption of fluids such as blood, but the material of the probe also decreases the drying time. Since enzymes in bodily fluids such as blood deteriorate the samples and drying renders the enzymes inactive. Further, the probe may be pre-treated with a material to retard enzyme action on the absorbed blood. Applying Urea to the probe and drying it is believed useful for enzyme inhibition. Applying a weak acid is also believed suitable if the acid is selected so it does not degrade the absorbed sample. Various protease inhibitors and inhibitor cocktails are available and could be applied to and dried on the probe 18, 118. For example, one protease inhibitor provided by Sigma Aldrich uses a combination of AEBSF (2 mM), Aprotinin (0.3 µM), Bestatin (130 µM), EDTA (1 mM), E-64 (14 µM) and Leupeptin (1 µM).

One purpose for these treatments is to prepare the sample for analysis, or to eliminate steps prior to analysis. Another common method of sample preparation is solid-phase extraction. The structure of the probe and the methods used in forming the probe 18, 118 allow for incorporation of sorbent particles (both silica and polymeric) that can capture analytes of interests during the drying step and then release them only under specific extraction conditions. Due to the specific nature of the extraction conditions, the probe can be washed with a variety of solvents that will remove interfering components from the biological fluid on the probe 18, 118. Then when the analyte of interest is extracted from the probe the sample that is extracted will be free of interfering biological matrix components.

As an example, microspheres in the 20-50 micron size range can be incorporated into the probe 18, 118 during formulation of the probe or by treatment after formation. Other sizes of particles may be used depending on the application, with microspheres as of about 120 microns in diameter being believed suitable. These microspheres could contain a high density of hydrophobic ligands on their surface, and will interact strongly with hydrophobic analytes such as Vitamin-D and its metabolites. When blood is collected onto such a treated probe 18, 118, the free analyte will partition onto the hydrophobic surface. During extraction, the analyte can only be extracted from the probe with non-polar solvents. So, the probe can be washed with aqueous solvents or mixtures of aqueous and organic solvents without removing the hydrophobic analyte. When washing is complete the hydrophobic analyte can be eluted with a strong organic extraction solvent.

The above description maintains the probe 18, 118 on the holder 114 during use. It is believed possible to remove the absorbent probe 18, 118 from the holder for extraction of the sample and analysis, but that is not believed as efficient from a time viewpoint. The holder 114 and probe are a single unit handled by the user, and have no individual protective sheath enclosing all or a substantial portion of the holder, and do not have the holder 114 reciprocating within an enclosing protective cover during use.

As used herein, the term "about" encompasses a variation of plus or minus 10%. While the above disclosure refers to absorbing various volumes of fluids within specified times, or less, one skilled in the art would understand that the larger end of the volume range cannot be absorbed within the minimum end of the time range. Thus, descriptions such as absorbing a specified range of blood in five seconds or less is to be construed rationally to encompass what may be practically achieved by the materials now available, and to the extent permitted by law while not invalidating the claims, construed to encompass what may be achievable by materials developed in the future.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The above description is given by way of example, and not limitation. Given the above disclosure, one skilled in the art could devise variations that are within the scope and spirit of the invention, including various ways of enclosing the device 10 or holder 114 in a protective case 10, and various ways of configuring the sample end 12 or probe 114. Moreover, while the preferred use of the holder 114 and probe 18, 118 is to absorb blood, its use is not so limited as the method and apparatus disclosed herein may be used to absorb, dry and transport other fluids. Further, the various features of this invention can be used alone, or in varying combinations with each other and are not intended to be limited to the specific combination described herein. Moreover, while the above described method and apparatus is preferably used to sample and test human blood, it may be used to sample and test blood from any animal. Moreover, the method and apparatus may be used to sample and test human and animal bodily fluids other than blood, and may further be used to sample and test any fluid. Thus, the invention is not to be limited by the illustrated embodiments.

What is claimed is:

1. A kit for collecting bodily fluid, comprising:
a plurality of holders each having an elongated and tapered body extending along a longitudinal axis and having a smaller diameter first end and an opposite, larger diameter second end, the second end forming a conical internal recess which recess extends along a first length of the longitudinal axis that includes at least the second end;
an absorbent probe at the first end of the body;
a container having a first container portion defining part of two to four separate compartments with each compartment receiving and enclosing a different one of the bodies with each body extending along a compartment longitudinal axis when the entire body and probe are enclosed within the different one of the compartments, each compartment having a wall located to abut a position stop on the holder to position the holder relative to the compartment's longitudinal axis so the absorbent probe does not contact the container;
a conical projection in each compartment extending along the compartment's longitudinal axis and sized to mate with the conical internal recess of the holder when the holder is placed in one of the compartments.

2. The kit of claim 1, wherein the absorbent probe is made of a material of sufficient size to absorb for analysis a maximum of about 20 µl of blood in about 2-5 seconds without separating the blood from plasma, the probe having a length of less than about 5 mm and a cross-sectional area of less than about 20 mm2 and a density of less than about 4 g/cc with a majority of the exterior surface of the probe being exposed and available for placing against a fluid sample on a surface to absorb the sample.

3. The kit of claim 2, wherein the absorbent probe is inserted into an open end of the body.

4. The kit of claim 2, wherein an end of the absorbent probe surrounds a portion of the body.

5. The kit of claim 2, wherein, the absorbent probe has a rounded distal end.

6. The kit of claim 1, wherein the tapered body has an outer surface with a circular cross-sectional shape at the second end and extending from the second end along the longitudinal axis toward the first end, with each of the ribs ending at the beginning of the outer surface with a circular cross-sectional shape.

7. The kit of claim 1, wherein the first length extends the entire length of the body.

8. The kit of claim 1, wherein the position stop comprises a notch in each rib.

9. The kit of claim 1, wherein the absorbent probe further comprises a surfactant adsorbed onto the surface of the absorbent probe.

10. The kit of claim 1, further comprising a first portion of a snap lock connection on each container compartment and a second portion of a snap lock connection on the second end of the holder.

11. A kit for collecting bodily fluid, comprising:
a plurality of holders having an elongated and tapered body extending along a longitudinal axis and having a smaller diameter first end and an opposite, larger diameter second end, the second end forming a conical internal recess which recess extends along a first length of the longitudinal axis;
an absorbent probe at the first end of the body;
three ribs each extending outward from the elongated body beginning adjacent the first end and extending along a second length of the elongated body, each rib having an outwardly extending position stop facing the first end at the same location along the longitudinal axis;
a container having first and second container portions which when joined together define only two to four separate compartments with each compartment receiving and enclosing a different one of the holders each extending along a compartment longitudinal axis when the entire holder is enclosed within the different one of the compartments, each compartment having a wall located to abut the position stop to position the holder relative to the compartment's longitudinal axis so the absorbent probe does not contact the container;
the second length having a distal end adjacent the absorbent material when the holders are in their respective compartments, with a plurality of ventilation openings on the distal end or a sidewall adjacent the distal end, with each ventilation opening associated with a different one of the compartments to allow air to enter the compartment associated with the ventilation opening.

12. The kit of claim 11, further comprising a conical projection in each compartment extending along the compartment's longitudinal axis and sized to mate with the conical internal recess of the body when the body is enclosed in one of the compartments.

13. The kit of claim 11, wherein the opening is in the distal end of the second length.

14. The kit of claim 11, wherein the opening is in the sidewall of the second length.

15. The kit of claim 11, wherein the container is rectangular.

16. The kit of claim 11, wherein the absorbent probe is made of a material of sufficient size to absorb for analysis a maximum of about 20 µl of blood in about 2-5 seconds without separating the blood from plasma, the probe having a length of less than about 5 mm and a cross-sectional area of less than about 20 mm2 and a density of less than about 4 g/cc with a majority of the exterior surface of the probe being exposed and available for placing against a fluid sample on a surface to absorb the sample.

17. The kit of claim 16, wherein the absorbent probe is inserted into an open end of the body.

18. The kit of claim 16, wherein an end of the absorbent probe surrounds a portion of the body.

19. The kit of claim 16, wherein, the absorbent probe has a rounded distal end.

* * * * *